(12) United States Patent
Webster et al.

(10) Patent No.: US 11,207,439 B2
(45) Date of Patent: Dec. 28, 2021

(54) SCENT DISPENSER/ABSORBER

(71) Applicant: NOVIA PRODUCTS, LLC, Portland, ME (US)

(72) Inventors: William Webster, Portland, ME (US); Randy M. Oliver, Limerick, ME (US); David Gallant, Newfield, ME (US)

(73) Assignee: NOVIA PRODUCTS, LLC, Portland, ME (US)

( * ) Notice: Subject to any disclaimer, the term of this patent is extended or adjusted under 35 U.S.C. 154(b) by 278 days.

(21) Appl. No.: 16/401,043

(22) Filed: May 1, 2019

(65) Prior Publication Data
US 2019/0336637 A1 Nov. 7, 2019

Related U.S. Application Data

(60) Provisional application No. 62/665,489, filed on May 1, 2018, provisional application No. 62/798,635, filed on Jan. 30, 2019.

(51) Int. Cl.
*A61L 9/12* (2006.01)

(52) U.S. Cl.
CPC ............ *A61L 9/12* (2013.01); *A61L 2209/133* (2013.01); *A61L 2209/134* (2013.01)

(58) Field of Classification Search
CPC .. A61L 9/12; A61L 2209/13; A61L 2209/133; A61L 2209/134
USPC ...................................... 239/51.5, 58, 59, 60
See application file for complete search history.

(56) References Cited

U.S. PATENT DOCUMENTS

| 1,481,325 | A | 1/1924 | Le Gris |
| 1,924,823 | A | 8/1933 | Willi |
| 2,234,062 | A | 3/1941 | Roberts |
| 2,763,395 | A | 9/1956 | Meek |

(Continued)

FOREIGN PATENT DOCUMENTS

| EP | 0335669 | 6/1993 |
| EP | 0691113 | 1/1996 |

OTHER PUBLICATIONS

U.S. Appl. No. 29/678,613, filed Jan. 30, 2019.
(Continued)

*Primary Examiner* — Jason J Boeckmann
(74) *Attorney, Agent, or Firm* — Lewis Roca Rothgerber Christie LLP

(57) ABSTRACT

A scent absorber/dispenser is disclosed. The scent dispenser/absorber has a housing having a base and a cover that cooperate to form an interior chamber of the housing. The dispenser can take the form of an individual dispenser/absorber housing, or a dual dispenser absorber made of two housings are arranged in piggyback (i.e., back-to-back) fashion. The interior chamber of each scent dispenser/absorber is configured to receive scent means adapted to perform either a scent-absorbing function or a scent-emitting function. To use the scent dispenser/absorber, the cover of one or more housings can be moved away from its respective base to expose diffusion ports in a sidewall of the base, thereby permitting desirable scents to flow from the corresponding scent means of the one or more housings to the surrounding environment, or undesirable odors in the surrounding environment to flow into the aforesaid scent means.

20 Claims, 14 Drawing Sheets

(56) References Cited

U.S. PATENT DOCUMENTS

| | | | |
|---|---|---|---|
| 3,286,872 A * | 11/1966 | Burdick, Jr. | A01M 1/10 220/351 |
| 3,873,281 A | 3/1975 | Himes et al. | |
| 3,888,416 A | 6/1975 | Lin | |
| 4,014,501 A * | 3/1977 | Buckenmayer | B65D 85/00 239/58 |
| D250,801 S | 1/1979 | Bergen et al. | |
| 4,137,200 A | 1/1979 | Wood et al. | |
| 4,146,566 A | 3/1979 | Gaiser | |
| 4,200,229 A | 4/1980 | Spector | |
| 4,327,056 A | 4/1982 | Gaiser | |
| 4,549,693 A * | 10/1985 | Barlics | A61L 9/12 206/0.5 |
| 4,815,659 A * | 3/1989 | Turko | A01M 1/2038 239/6 |
| 4,869,407 A | 9/1989 | Booth, Jr. et al. | |
| 4,957,810 A | 9/1990 | Eleouet et al. | |
| 5,064,653 A | 11/1991 | Sessions et al. | |
| D351,650 S | 10/1994 | Vavra | |
| 5,388,762 A | 2/1995 | Bryson, Sr. | |
| D372,770 S | 8/1996 | Foreman | |
| 5,610,674 A | 3/1997 | Martin | |
| 5,611,165 A * | 3/1997 | Blaha | A01M 31/008 239/58 |
| D387,734 S | 12/1997 | Hawkins, Jr. et al. | |
| 5,837,377 A | 11/1998 | Sheu et al. | |
| 5,880,216 A | 3/1999 | Tanihara et al. | |
| 5,898,475 A | 4/1999 | Martin | |
| 5,973,221 A | 10/1999 | Collyer et al. | |
| D422,481 S | 4/2000 | Bertani | |
| 6,277,401 B1 | 8/2001 | Bello et al. | |
| 6,617,014 B1 | 9/2003 | Thomson | |
| D493,875 S | 8/2004 | Groene et al. | |
| 6,889,870 B2 | 5/2005 | De Laforcade | |
| 6,991,848 B2 | 1/2006 | Thomson | |
| 6,997,355 B2 | 2/2006 | Duquet et al. | |
| 7,048,966 B2 | 5/2006 | Thomson | |
| D550,840 S | 9/2007 | Anderson et al. | |
| D568,715 S | 5/2008 | Gustafson et al. | |
| D575,711 S | 8/2008 | Johannsen | |
| 8,251,299 B1 * | 8/2012 | Irvin | A61L 9/048 239/58 |
| D676,551 S | 2/2013 | Desai et al. | |
| 8,544,766 B2 | 10/2013 | Webster et al. | |
| D710,699 S | 8/2014 | Phelps | |
| D791,426 S | 7/2017 | Petersen | |
| D794,765 S | 8/2017 | Brandenburg et al. | |
| D830,530 S | 10/2018 | Webster et al. | |
| 2002/0018884 A1 | 2/2002 | Thomson | |
| 2002/0113909 A1 | 8/2002 | Sherwood | |
| 2004/0144811 A1 | 7/2004 | Pennaneac'H | |
| 2006/0216492 A1 | 9/2006 | Thomson | |
| 2007/0187524 A1 | 8/2007 | Sherwood | |
| 2007/0224232 A1 | 9/2007 | Sherwood | |
| 2011/0147478 A1 | 6/2011 | Bernstein | |
| 2013/0206861 A1 | 8/2013 | Webster et al. | |
| 2017/0312380 A1 | 11/2017 | Webster et al. | |
| 2019/0125916 A1 | 5/2019 | Webster et al. | |

OTHER PUBLICATIONS

U.S. Appl. No. 62/480,948, filed Apr. 3, 2017.
www.scentair.com/products/index.php?subSectionID=2.
ScentWave SWD-1000 Technical Specifications.
ScentStream SXD-5020 Technical Specifications.
ScentPOP Technical Specifications.

* cited by examiner

US 11,207,439 B2

SCENT DISPENSER/ABSORBER

CROSS-REFERENCE TO RELATED APPLICATION

This application claims priority to U.S. Provisional Patent Application Ser. No. 62/665,489 filed May 1, 2018 and U.S. Provisional Patent Application Ser. No. 62/798,635 filed Jan. 30, 2019, the entire disclosures of which are incorporated herein by reference.

FIELD OF INVENTION

The disclosed subject matter relates to dispensers of scents into the environment and/or absorbers of odors or materials from the environment.

BACKGROUND OF THE INVENTION

Many forms of dispensers of scents into the environment, such as household or other building interior environments, or devices for removing odors or materials from such environments, are known in the art. Commonly, annoying situations arise due to various undesirable odors in the air, which are commonly resolved either by removing the odor or masquerading it with, for example, scents having a desirable fragrance. Additionally, situations may also arise in which it is advantageous to scent the air in general, such as for branding purposes or for sampling scents. In order to achieve the foregoing objectives, various scent-dispensing devices have been developed for use with perfumes, flower essences or other air fresheners. However, the beneficial effects of these prior devices have frequently been prone to vanish or vaporize within a very short time span.

SUMMARY OF THE INVENTION

The present invention relates to a scent dispenser/absorber adapted for quick and easy manual actuation. More particularly, and in accordance with a first embodiment of the present invention, the inventive scent dispenser/absorber disclosed herein comprises a housing having a base and a cover that cooperate to form an interior chamber of the housing. An insert, which, for example, can be adapted to absorb or adsorb a volatile scented substance, is sized and shaped such that it may be positioned in the interior chamber of the housing. The base and cover are movable toward and away from each in a rectilinear (i.e., axial), telescoping-like fashion. In operation, the cover can be moved away from the base in an axial direction to expose diffusion ports in a sidewall of the cover, thereby permitting the scent of the volatile substance contained in the insert to exit from the housing and enter the surrounding environment for any one of myriad purposes. When the base and cover of the housing are in a completely extended axial position, desirable scents can also flow out of slots provided in a lower rim of the cover, providing increased scent diffusion and a more even peripheral distribution of scents.

In accordance with a second embodiment of the present invention, the inventive scent dispenser/absorber disclosed herein comprises a pair of housings, each housing having a base and a cover that cooperate to form an interior chamber. The housings are arranged in piggyback (i.e., back-to-back) fashion such that the scent dispenser has a pair of interior chambers, each chamber being sized and shaped to receive scent means adapted to perform either a scent-absorbing function or a scent-emitting function. The base and cover of each housing are movable toward and away from each other in a rectilinear (i.e., axial), telescoping-like fashion.

In operation, the cover of a first one of the housings can be moved away from its respective base to expose diffusion ports in a sidewall of that particular cover, thereby permitting (i) desirable scents to flow from the scent means of the first one of the housings to the surrounding environment or (ii) undesirable odors in the surrounding environment to flow into the scent means of the first one of the housings, where they can be absorbed. Similarly, the cover of a second one of the housings can be moved away from its respective base to expose diffusion ports in a sidewall of that particular cover, thereby permitting (iii) desirable scents to flow from the scent means of the second one of the housings to the surrounding environment or (iv) undesirable odors in the surrounding environment to flow into the scent means of the second one of the housings, where they can be absorbed. When the base and cover of the first one of the housings are in a completely extended axial position, desirable scents can also flow out of slots provided in a lower rim of the corresponding cover, providing increased scent diffusion and a more even peripheral distribution of scents. When the base and cover of the second one of the housings are in a completely extended axial position, desirable scents can also flow out of slots provided in a lower rim of the corresponding cover, providing increased scent diffusion and a more even peripheral distribution of scents.

When there are two housings, as is the case with the second embodiment described hereinabove, the scent dispenser/absorber can be extremely versatile. For instance, and by way of example, one housing can be in a scent-emitting mode, while the other housing is in an odor-absorbing mode. By way of further example, both housings can be in a scent-emitting mode, thereby providing two additional options (i.e., one in which two different scents are emitted simultaneously and another in which the same scent is emitted from both housings). If and when the surrounding environment is heavily laden with undesirable odors, both housings can be in an odor-absorbing mode.

BRIEF DESCRIPTION OF THE DRAWINGS

For a better understanding of the present invention, reference is made to the following detailed description of various exemplary embodiments considered in conjunction with the accompanying drawings, in which like structures are referred to by the like reference numerals throughout the several views, and in which.

DETAILED DESCRIPTION OF THE INVENTION

With initial reference to FIGS. 1-6, they represent views of a scent dispenser 10 constructed according to an exemplary embodiment of the present invention, including its various elements. However, consistent with the nature of such views, some elements of the scent dispenser 10 described herein may not be visible in those figures. All relevant elements of the scent dispenser 10 are discussed further hereinbelow.

When considering FIGS. 1-6, it should be understood that terms indicating position, orientation or direction of motion are used throughout the discussion of these figures in relation to the disclosed elements and are consistent with the position, orientation or direction of the various elements shown therein, unless otherwise expressly noted. Such terms are used for the purpose of facilitating discussion, and not to limit the exemplary embodiment to the particular terms described herein or to limit physical orientation in actual use to any particular coordinate system (e.g., horizontal, vertical and front, back and side), during actual use of the scent dispenser 10.

Figure 2:
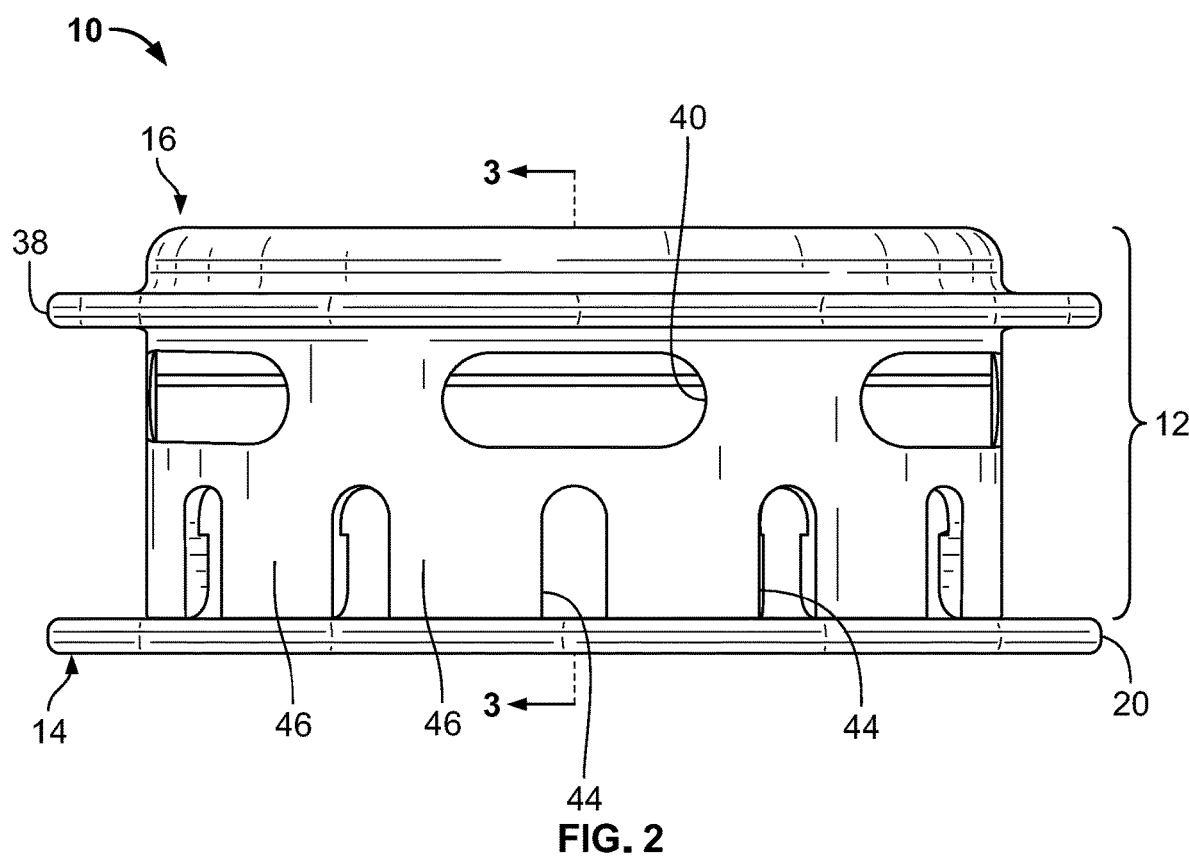
FIG. 2 is a side elevational view of the scent dispenser illustrated in FIG. 1.
Figure 3:
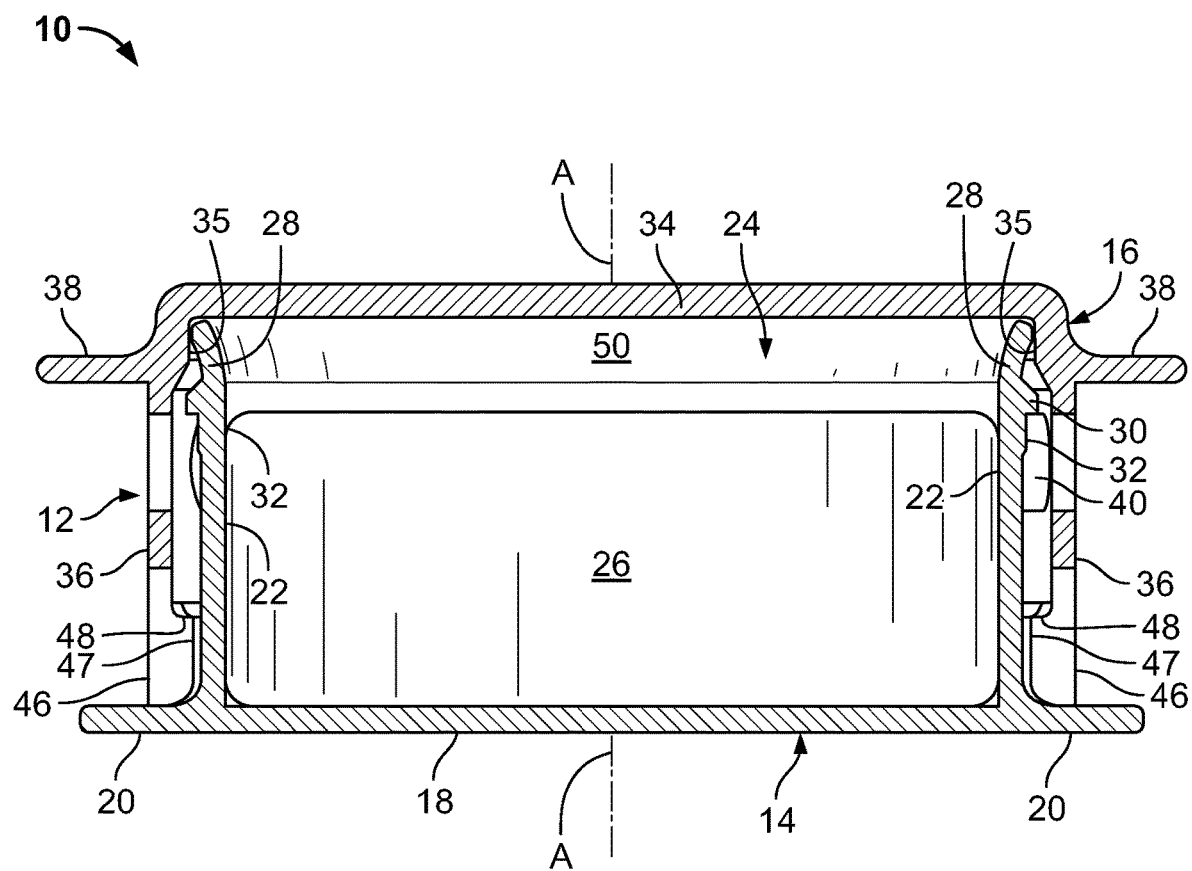
FIG. 3 is a cross-sectional view, taken along section line 3-3 in FIG. 2 and looking in the direction of the arrows, showing the interior of the scent dispenser of FIG. 2 when it is in its closed (i.e., non-scent dispensing) position or condition.
Figure 4:
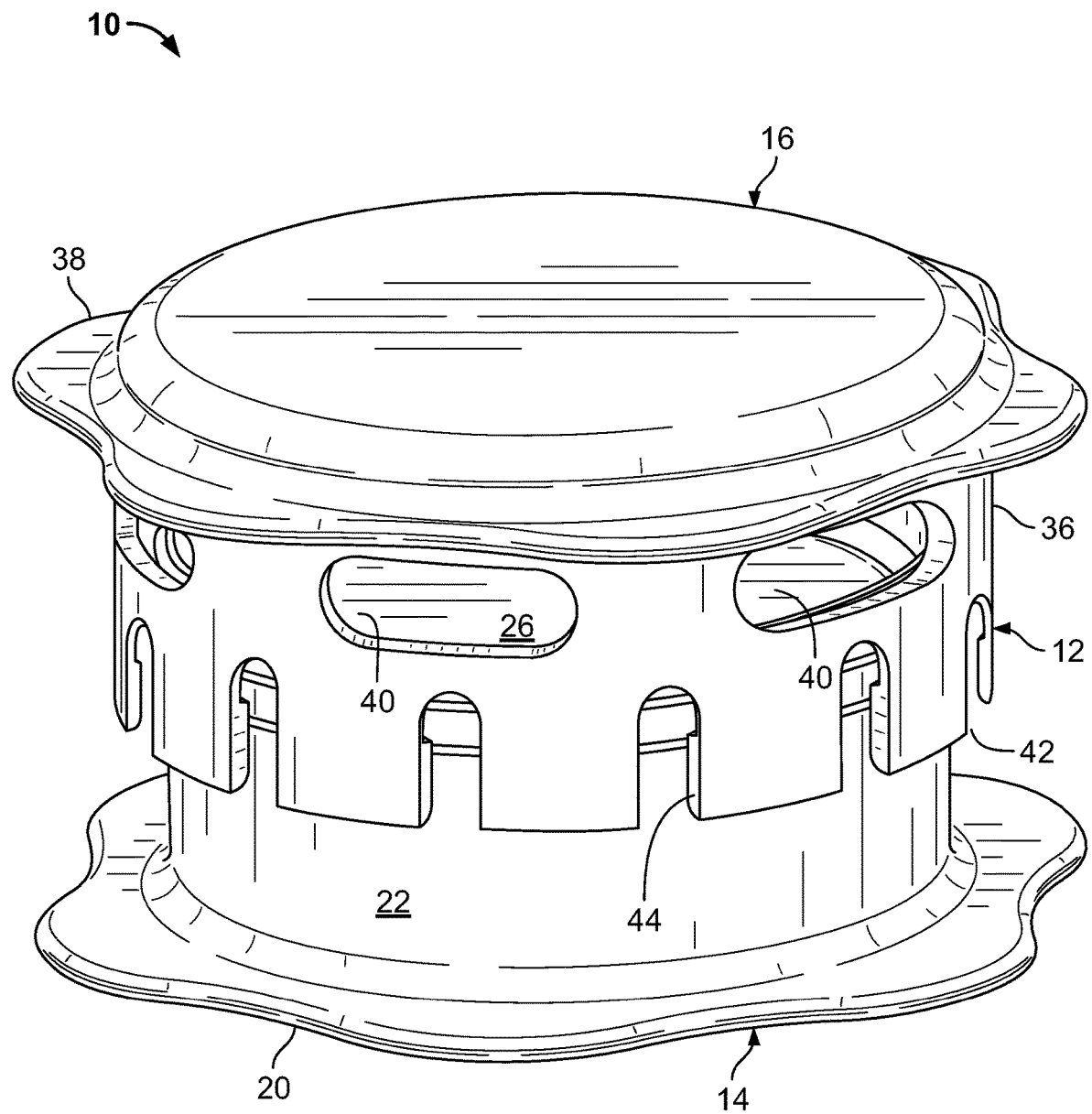
FIG. 4 is a top perspective view of the scent dispenser of FIG. 1, the dispenser being shown in an open (i.e., scent dispensing) position or condition and with its base and cover in an expanded state, rather than in the contracted state depicted in FIG. 1.
Figure 5:
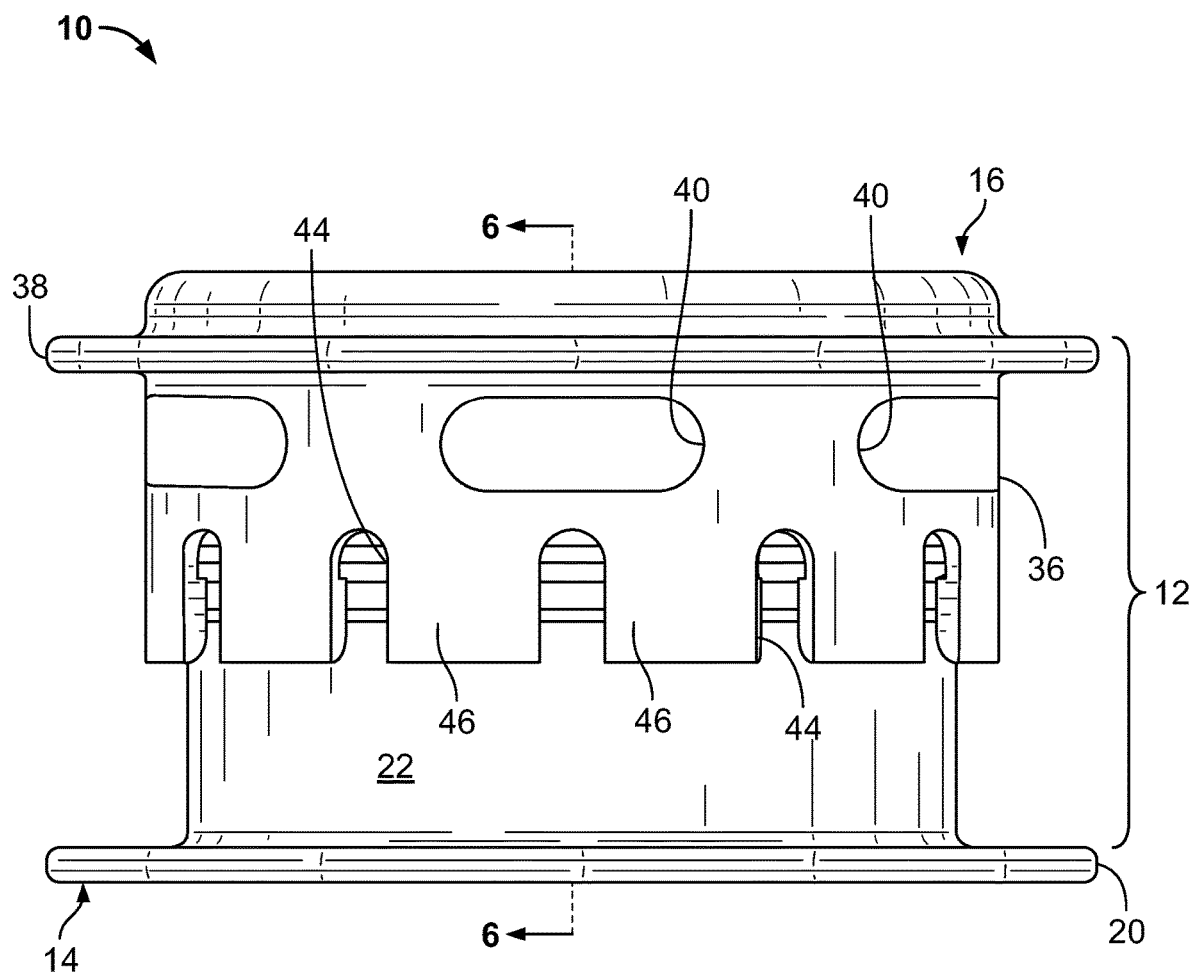
FIG. 5 is a side elevational view of the scent dispenser illustrated in FIG. 2, but with its base and cover in an expanded state, rather than in the contracted state depicted in FIG. 2.
Figure 6:
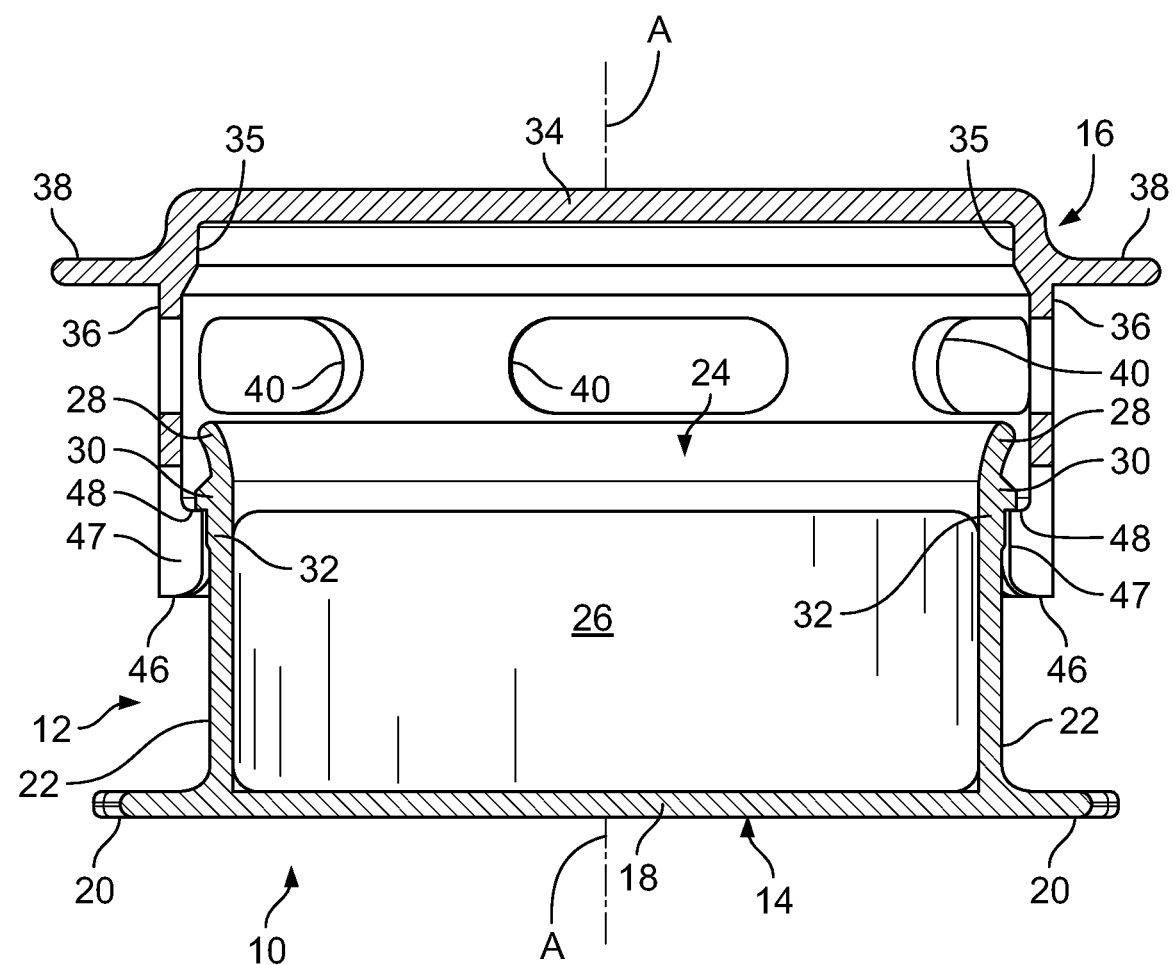
FIG. 6 is a cross-sectional view, taken along section line 6-6 in FIG. 5 and looking in the direction of the arrows, showing the interior of the scent dispenser of FIG. 5 when it is in its open (i.e., scent dispensing) position or condition.

With the foregoing prefatory comments in mind, and with continued reference to FIGS. 1-6, the scent dispenser 10 mentioned in the preceding paragraph includes a housing 12 formed by a base 14 and a cover 16, which is slidably movable along a longitudinal axis A (see FIGS. 3 and 6) in a rectilinear (i.e., axial), telescoping-like fashion relative to the base 14, between a retracted position (see FIGS. 1-3) and a completely extended position (see FIGS. 4-6). The base 14 and the cover 16 are also rotatable relative to one another as indicated above, whereby they may assume various different rotational orientations relative to each other.

The base 14, which can, for example, be molded monolithically from polypropylene or any other suitable material, has a substantially flat bottom surface (i.e., support surface) 18. An annular flange 20 projects radially outwardly from the bottom surface 18 of the base 14. The flange 20, which has a scalloped design to facilitate gripping by a user's hand, extends around the entire circumference of the base 14.

The base 14 also has a solid (i.e., uninterrupted), cylindrical sidewall 22 extending upwardly from the bottom surface 18 of the base 14 and cooperating with the bottom surface 18 to form an interior chamber 24 having an open upper end and a lower end that is closed by the bottom surface 18 of the base 14. The interior chamber 24 is sized and shaped to receive a round, disc-like insert 26 made of foam or any other suitable material (e.g., a piece of medical grade hydrophilic polyurethane, preferably non-reticulated and about 3/16 of an inch in thickness) adapted to absorb or adsorb a volatile scented substance.

The sidewall 22 is provided with an outwardly flared upper rim 28 and an annular flange 30, which projects radially outwardly from the sidewall 22 in proximity to the upper rim 28. Both the upper rim 28 and the annular flange 30 extend around the entire circumference of the sidewall 22. An annular band 32 also extends around the entire circumference of the sidewall 22. The annular band 32 is positioned on the sidewall 22 adjacent the annular flange 30. More particularly, the annular band 32 is located on the side of the annular flange 30 opposite from the side that is proximate the upper rim 28. The annular band 32 projects radially outwardly from the sidewall 22 a distance that is less than the distance that the annular flange 30 projects from the sidewall 22.

The cover 16, which can also be molded monolithically from polypropylene or any other suitable material, has a substantially flat top surface (i.e., closed end) 34 and a cylindrical sidewall 36 extending downwardly from the top surface 34 of the cover 16. An annular flange 38 projects radially outwardly from the sidewall 36 of the cover 16. The flange 38, which has a scalloped design to facilitate gripping by another hand of the user, extends around the entire circumference of the sidewall 36.

Figure 1:
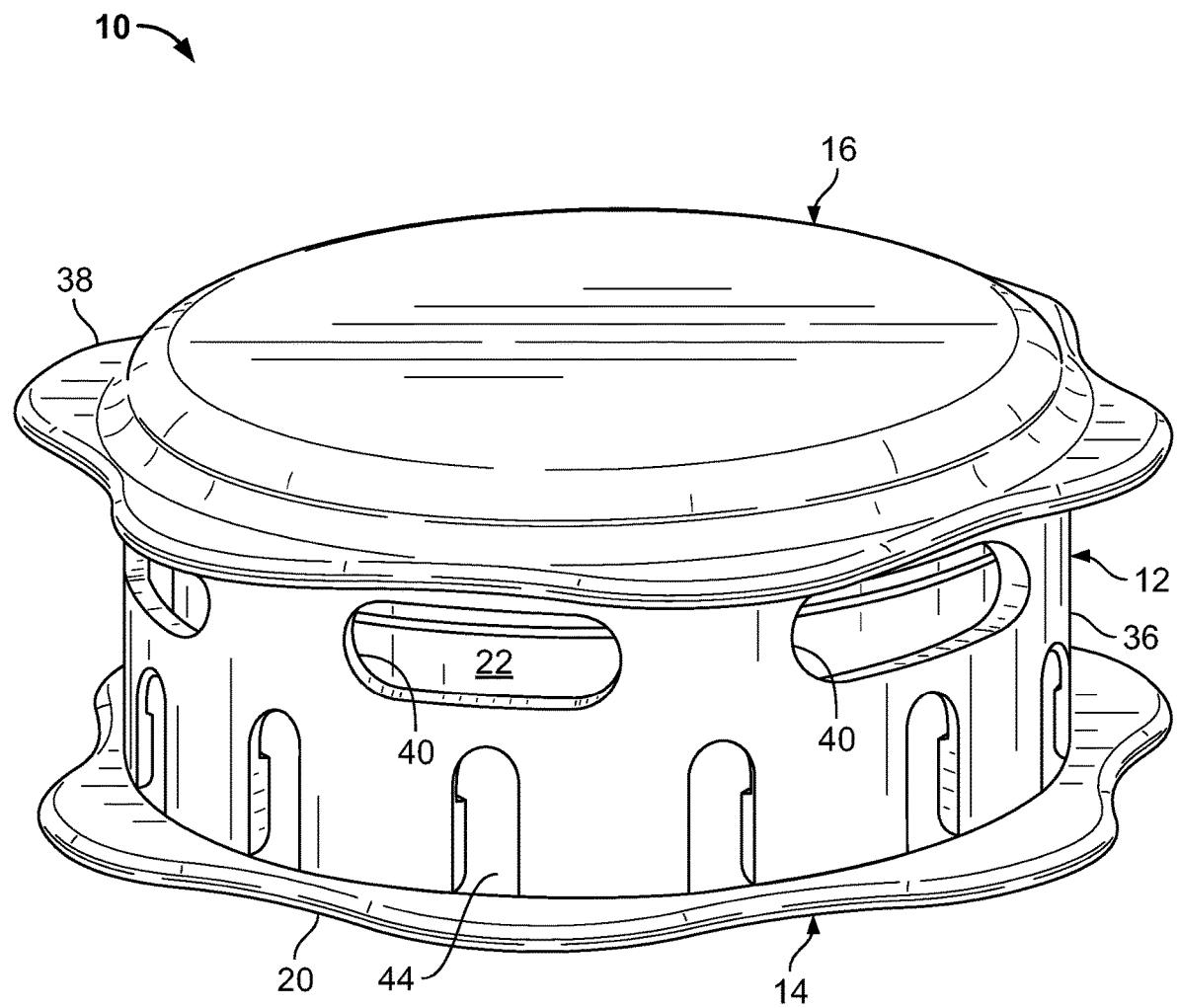
FIG. 1 is a top perspective view of a scent dispenser constructed in accordance with an embodiment of the present invention, the illustrated dispenser being shown in a closed (i.e., non-scent dispensing) position or condition and with its base and cover in a contracted state and in a particular rotational orientation relative to one another.

The sidewall 36 of the cover 16 is also provided with a plurality of diffusion ports 40, each of which has a generally oval or oblong shape. The diffusion ports 40 are spaced apart around the circumference of the sidewall 36 in proximity to the annular flange 38. More particularly, the diffusion ports 40 are located on the side of the annular flange 38 opposite from the side that is proximate to the top surface 34 of the cover 16. When the scent dispenser 10 is in its closed position or condition as shown in FIGS. 1-3, the annular flanges 20, 38 project outwardly from the sidewall 36 of the cover 16 approximately the same distance. However, in another embodiment, one of the flanges 20, 38 could project farther than the other one.

The sidewall 36 has a lower rim 42 provided with a plurality of slots 44, each of which has a shape that resembles an inverted "U." The slots 44 are spaced apart around the circumference of the sidewall 36, some in alignment with (i.e., directly underneath) the diffusion ports 40 and some in between the diffusion ports 40. The slots 44 form a plurality of fingers 46 therebetween. Each of the fingers 46 is provided with a radially inwardly projecting pad 47 forming a shoulder 48 (see especially FIGS. 3 and 6).

The slots 44 and diffusion ports 40 can be located at various different angular positions around the periphery (i.e., circumference) of the sidewall 36 and lower rim 42. For example, diffusion ports 40 can be located at 90°, 180°, 270°, and 360° along the circumference of housing 12, while slots 44 may be located at 45°, 135°, 225° and 315°. While the exemplary embodiments described hereinabove have the diffusion ports 40 and slots 44 oriented in a symmetrical fashion about the circumference of base 14, in other embodiments the diffusion ports 40 and slots 44 can be oriented in an asymmetrical fashion.

With the cover 16 removed from the base 14 to thereby provide access to the interior chamber 24 of the housing 12, the insert 26 can be placed in the interior chamber 24, where it would rest on the bottom surface 18 of the base 14. Either before or after the aforementioned insertion step, any desired number of drops of a suitable odorant would be applied to the insert 26 from, for instance, a conventional droplet dispenser. After the aforementioned odorant application step, the cover 16 of the housing 12 would be applied to the base 14 and moved to its retracted position (see FIGS. 1-3), in which the scent dispenser 10 would be in its closed position or condition. The application of the cover 16 to the base 14 is facilitated by the slots 44, which render the lower rim 42 of the cover 16 resilient enough to flex radially outwardly in response to contact by the flared upper rim 28 and the annular flange 30 of the base 14.

When the cover 16 is in its fully retracted position relative to the base 14 (i.e., when the scent dispenser 10 is in its closed position or condition), the upper rim 28 of the sidewall 22 of the base 14 contacts a radially inwardly extending flange 35 located at the juncture of the top surface 34 and sidewall 36 of cover 16 and cooperates with flange 35, which extends around the entire perimeter of sidewall 36, to form a water-tight or liquid-tight seal for the interior chamber 24. In other words, the upper rim 28 and the flange 35 function as sealing members. Also, when the cover 16 is in its fully retracted position, the diffusion ports 40 in its sidewall 36 are completely covered or blocked by the sidewall 22 of the base 14, whereby the interior chamber 24 is sealed off from the outside environment.

Conversely, when the cover 16 is in its completely extended position relative to the base 14 (i.e., when the scent dispenser 10 is in its open position or condition), the annular band 32 creates a slight friction fit with the pads 47 on the fingers 46 at the lower rim 42 of the cover 16 to thereby maintain the cover 16 in its completely extended position and, consequently, the scent dispenser 10 in its completely open position or condition in which the diffusion ports 40 are completely uncovered. When the scent dispenser 10 is in its aforesaid completely open position or condition, scent can also flow out of the slots 44, thereby increasing the amount of scent being dispensed. Because some of the slots 44 are angularly aligned with the diffusion ports 40 and some of the slots 44 are located between the diffusion ports 40 along the perimeter (i.e., circumference) of sidewall 36, scent is released or absorbed more evenly around the entire circumference of the housing 12.

It should be noted that the frictional forces produced by the contact between the annular band 32 and the pads 47 can be calculated such that the cover 16 is automatically maintained at any one of a number of variable (i.e., intermediate) positions relative to the base 14, thereby permitting a user to vary the uncovered portions of the diffusion ports 40 so as to regulate the dispersion of the scent emanating from the housing 12. Certain intermediate positions permit scent to flow out of slots 44 in addition to diffusion ports 40.

Likewise, the cover 16 may be rotated by a user to adjust it to any number of variable rotational positions relative to the base 14 to control the directionality of the scent emanating from the housing 12 through the diffusion ports 40 and/or the slots 44. The size, shape and number of the diffusion ports 40 and the slots 44 can be selected so as to further dictate the degree to which scent emanates from housing 12 when open, either completely or partially. The same parameters can also be manipulated to change the scent dispersion pattern of scent dispenser 10 when either completely or partially open. It should also be noted that the fully extended position of the cover 16 is delimited by the annular flange 30 on the sidewall 22 of the base 14, which functions as a stop when contacted by the shoulders 48 on the fingers 46 formed along the lower rim 42 of the cover 16. The annular flange 30 may also cooperate with the shoulders 48 to prevent the removal of the cover 16 from the base 14 or to make such removal possible, but difficult, or even easy.

When, for example, the insert 26 is made from a hydrophilic polyurethane material, the insert 26 would capture the odorant and allow odorant molecules, which are polar or near polar, to spread throughout the hydrophilic polyurethane material of the insert 26. With the scent dispenser 10 in its closed position or condition as shown in FIGS. 1-3, evaporation of the odorant molecules will be contained within the housing 12, thereby filling a headspace 50 between the insert 26 and the top surface 34 of the cover 16. In such a position and condition, the scent dispenser 10 is adapted for storage and/or transportation. Because any such hydrophilic polyurethane material (it being of medical grade) would have been reacted with water, the odorant scent released from the insert 26 into the headspace 50 of the housing 12 will not be adulterated by an additive in the manufacturing process. The result is that when the scent dispenser 10 is put in its open position or condition by moving the cover 16 to its extended position relative to the base 14 (see FIGS. 4-6), a faithful iteration of the original odorant scent will be released for sampling or other purposes. In other words, the aforementioned sampling step is carried out in an environment in which essentially ambient air contains scent molecules, but no liquid. Thus, the scent dispenser 10 allows scents to be stored, transported and/or sampled in a non-liquid form.

While the insert 26 has been described with reference to a specific embodiment thereof, it should be understood by those skilled in the art that various changes may be made and equivalents may be substituted without departing from the true spirit and scope of the present invention. For instance, the scent dispenser 10 is adapted for use with other types of scent capturing and diffusing media such as the scent cell disclosed in U.S. Patent Application Publication No. 2017/0312380 (see especially Paragraphs [0048] to [0050], U.S. Pat. No. 8,544,766 (see especially Column 6, lines 30-59) and U.S. Pat. No. 6,617,014, all of which patent publications are incorporated herein by reference in their entireties. In addition, many modifications may be made to the embodiment described herein to adapt it to a particular situation, use or application without departing from the overall objective, spirit and/or scope of the present invention. For instance, the insert 26 can be replaced by, for example, a scent cartridge adapted to absorb and/or adsorb a volatile scented substance, while allowing the ready passage of air therethrough. In some embodiments, the scent cartridge would contain an amount of volatile scented substance, such as those used in perfumes, for attracting game, for calming a pet, as diet aids, for aroma therapy, for medical applications, or for other uses which are known or may become known, such as providing cannabis-derived and/or hemp-derived scents, fragrances, etc. In some embodiments, the scent cartridge would be designed such that the scented substance may be added directly to the cartridge to replenish or change the scent.

By way of further example, the insert 26 may be made of any material that can carry and release volatile scented substances. In some embodiments, it could be made of an absorbent fibrous material or closed cell foam having air passages penetrating therethrough. In other embodiments, the insert 26 could be made of an open-cell foam that presents an appreciable ratio of surface area to volume of foam, with higher ratios typically being preferred. In such embodiments, the foam may be a hydrophilic foam or have a hydrophilic material exposed at the surfaces of its cells. Other suitable embodiments could utilize an open-cell foam composite made of substantially hydrophobic foam to provide structure to the composite and substantially hydrophilic foam exposed at the surfaces of its cells, such as the foam described in U.S. Pat. No. 6,617,014, whose disclosure is incorporated herein by reference in its entirety.

In yet other embodiments, the insert 26 may comprise a nonwoven fibrous material substrate coated with, for example, a substantially hydrophilic foam coating which is exposed at the surface and in interstitial spaces within the nonwoven fibrous material. The interstitial spaces within the nonwoven fibrous material form air passages penetrating therethrough to allow the flow of air. Examples of suitable nonwoven fibrous materials include, without limitation, cotton, felt, silk, or combinations thereof. As will be recognized by persons of ordinary skill in the relevant art, such embodiments would be useful when the volatile scented substances employed to impart scent or alternative odor to the insert 26 are of the types that may react with and degrade some hydrophobic foams (see, e.g., U.S. Pat. No. 8,544,766, which is incorporated herein by reference in its entirety). One possible process for producing such an insert 26 involves contacting a substrate of nonwoven fibrous material with a prepolymer emulsion and then polymerizing or curing the emulsion. By way of further example, the substrate can be dipped or immersed in the prepolymer emulsion, which can also be applied by brushing, spraying or otherwise coating onto the substrate. In an embodiment of such a process, the substrate of nonwoven fibrous material may be provided as a sheet or block and then sprayed with the prepolymer emulsion, followed by polymerization or curing of the emulsion to form the substantially hydrophilic foam on the nonwoven fibrous substrate. The substrate can then be cut into appropriately sized and shaped pieces to produce the insert 26.

Referring now to FIGS. 7-14, they represent views of a dual scent dispenser 110 constructed according to another exemplary embodiment of the present invention, in which there are a pair of housings 112, 212. Consistent with the nature of the views represented by FIGS. 7-14, some elements of the scent dispenser 110 described herein may not be visible in those figures. All relevant elements of the scent dispenser 110, including the housing 112 and the housing 212, are discussed further hereinbelow.

When considering FIGS. 7-14, it should be understood that terms indicating position, orientation or direction of motion are used throughout the discussion of these figures in relation to the disclosed elements and are consistent with the position, orientation or direction of the various elements shown therein, unless otherwise expressly noted. Such terms are used for the purpose of facilitating discussion, and not to limit the exemplary embodiment of FIGS. 7-14 to the particular terms described herein or to limit physical orientation in actual use to any particular coordinate system (e.g., horizontal, vertical and front, back and side). With the foregoing prefatory comments in mind, and with continued reference to FIGS. 7-14, the scent dispenser 110 will first be described with reference to the housing 112, followed by a description of the housing 212.

With particular and initial reference to the housing 112, it is formed by a base 114 and a cover 116, which is slidably movable along a longitudinal axis A' in a rectilinear (i.e., axial), telescoping-like fashion relative to the base 114, between a retracted position (see FIGS. 7-9) and a completely extended position (see FIGS. 10-14). The base 114 and the cover 116 are also rotatable relative to one another as indicated above, whereby they may assume various different rotational orientations relative to each other.

The base 114, which can, for example, be molded monolithically from polypropylene or any other suitable material, includes a substantially flat bottom surface (i.e., support surface) 118 (see FIGS. 9 and 14) and an annular flange 120 projecting radially outwardly from the bottom surface 118 of the base 114. The flange 120, which has a scalloped design to facilitate gripping by a user's hand, extends around the entire circumference of the base 114.

The base 114 also includes a solid (i.e., uninterrupted), cylindrical sidewall 122 extending upwardly from the bottom surface 118 of the base 114 and cooperating with the bottom surface 118 of the base 114 to form an interior chamber 124 (see FIGS. 9 and 14), having an open upper end and a lower end that is closed by the bottom surface 118 of the base 114. The interior chamber 124 is sized and shaped to receive a round, disc-like insert 126 (see FIGS. 9 and 14) made of foam or any other suitable material (e.g., a piece of medical grade hydrophilic polyurethane, preferably non-reticulated and about $3/16$ of an inch in thickness) adapted to absorb or adsorb a volatile scented substance.

The sidewall 122 is provided with an outwardly flared upper rim 128 (see FIGS. 9 and 14) and an annular flange 130 (see FIGS. 9 and 14), which projects radially outwardly from the sidewall 122 in proximity to the upper rim 128. Both the upper rim 128 and the annular flange 130 extend around the entire circumference of the sidewall 122. An annular band 132 also extends around the entire circumference of the sidewall 122. The annular band 132 is positioned on the sidewall 122 adjacent the annular flange 130. More particularly, the annular band 132 is located on the side of the annular flange 130 opposite from the side that is proximate the upper rim 128. The annular band 132 projects radially outwardly from the sidewall 122 a distance that is less than the distance that the annular flange 130 projects from the sidewall 122.

The cover 116, which can also be molded monolithically from polypropylene or any other suitable material, has a substantially flat top surface (i.e., closed end) 134 and a cylindrical sidewall 136 extending downwardly from the top surface 134 of the cover 116. An annular flange 138 projects radially outwardly from the sidewall 136 of the cover 116. The flange 138, which has a scalloped design to facilitate gripping by another hand of the user, extends around the entire circumference of the sidewall 136.

Figure 7:
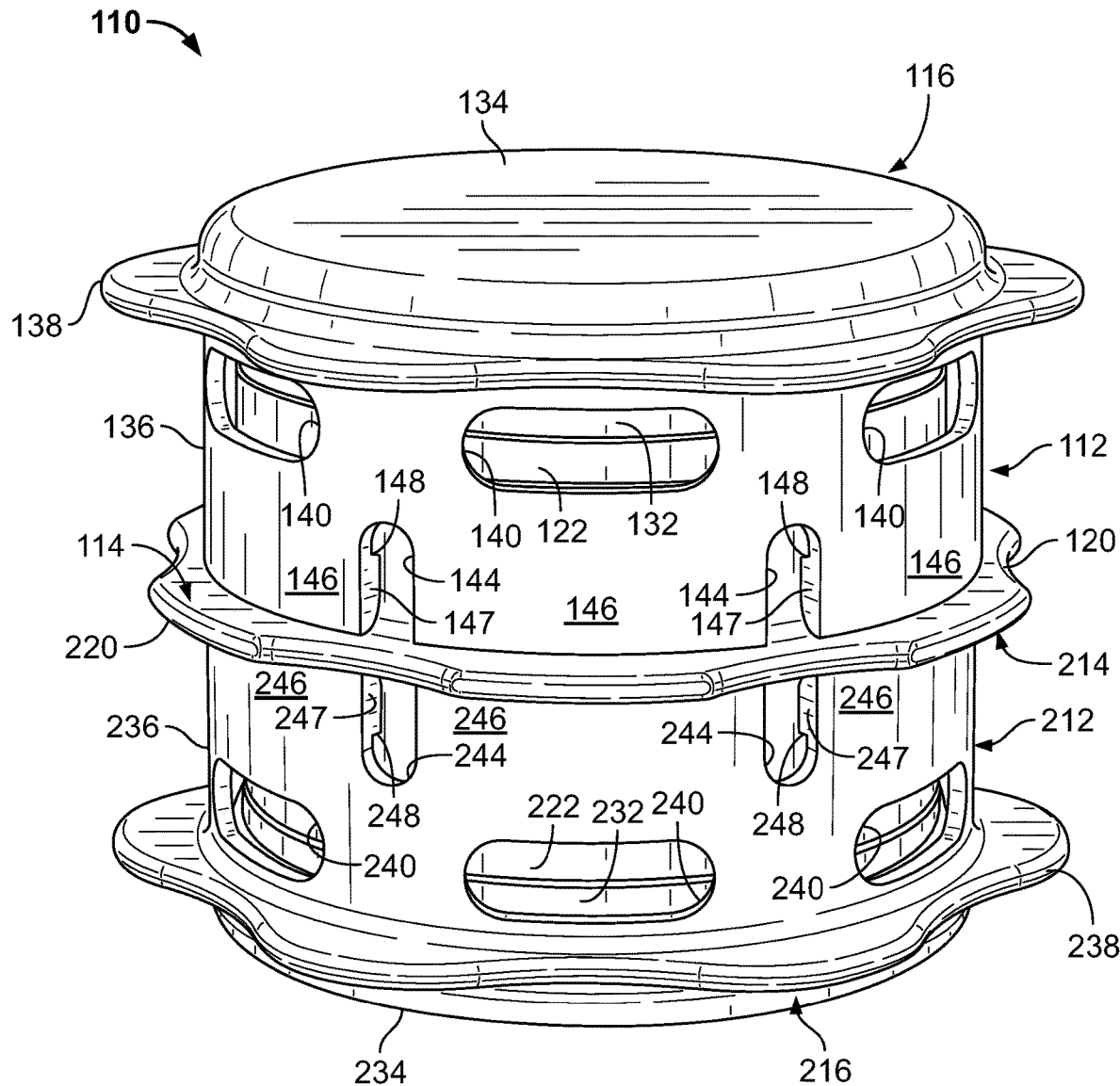
FIG. 7 is a top perspective view of a scent dispenser constructed in accordance with another embodiment of the present invention, the illustrated dispenser being shown in a closed (i.e., non-scent dispensing) position or condition and with its base and covers in a contracted state and in a particular rotational orientation relative to one another.
Figure 8:
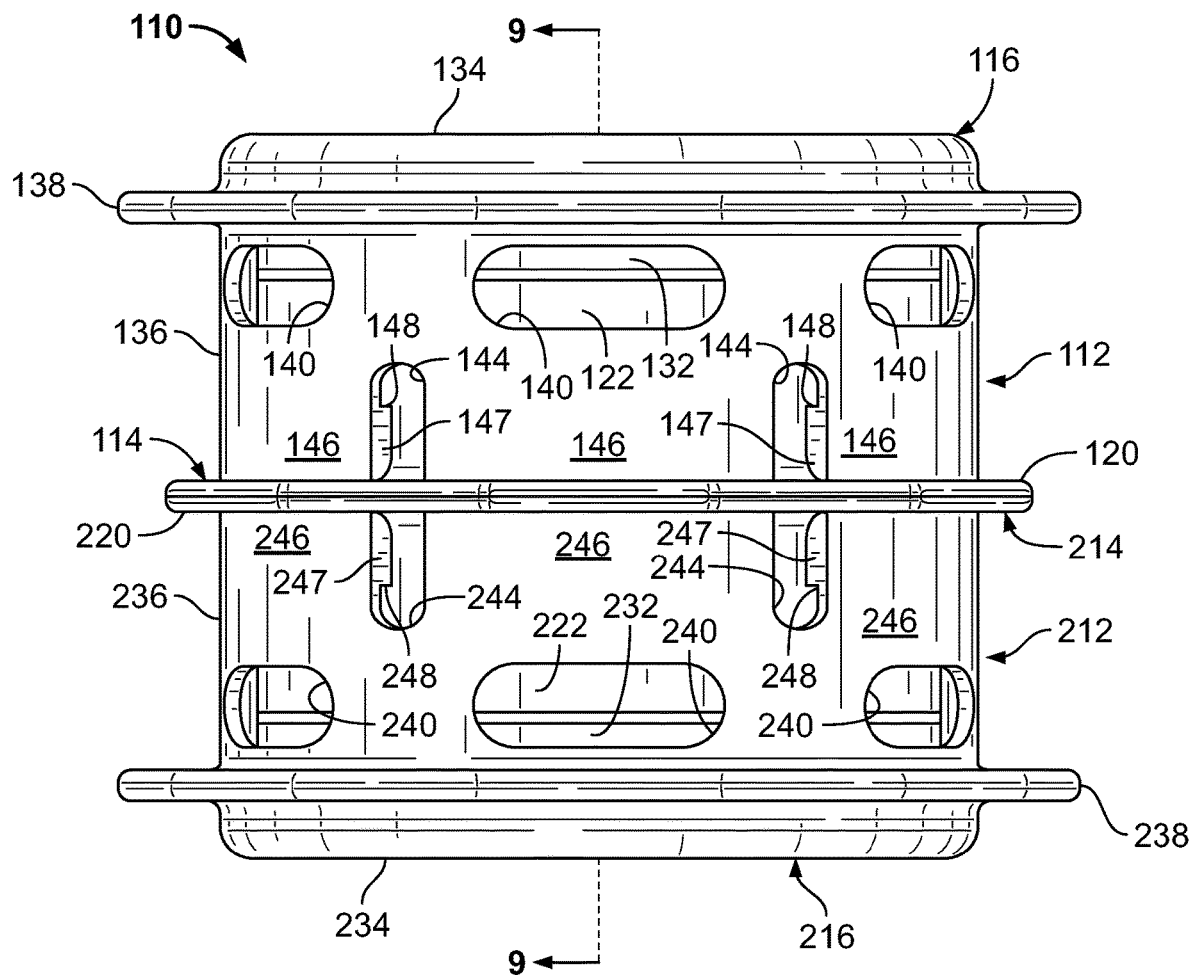
FIG. 8 is a side elevational view of the scent dispenser illustrated in FIG. 7.
Figure 9:
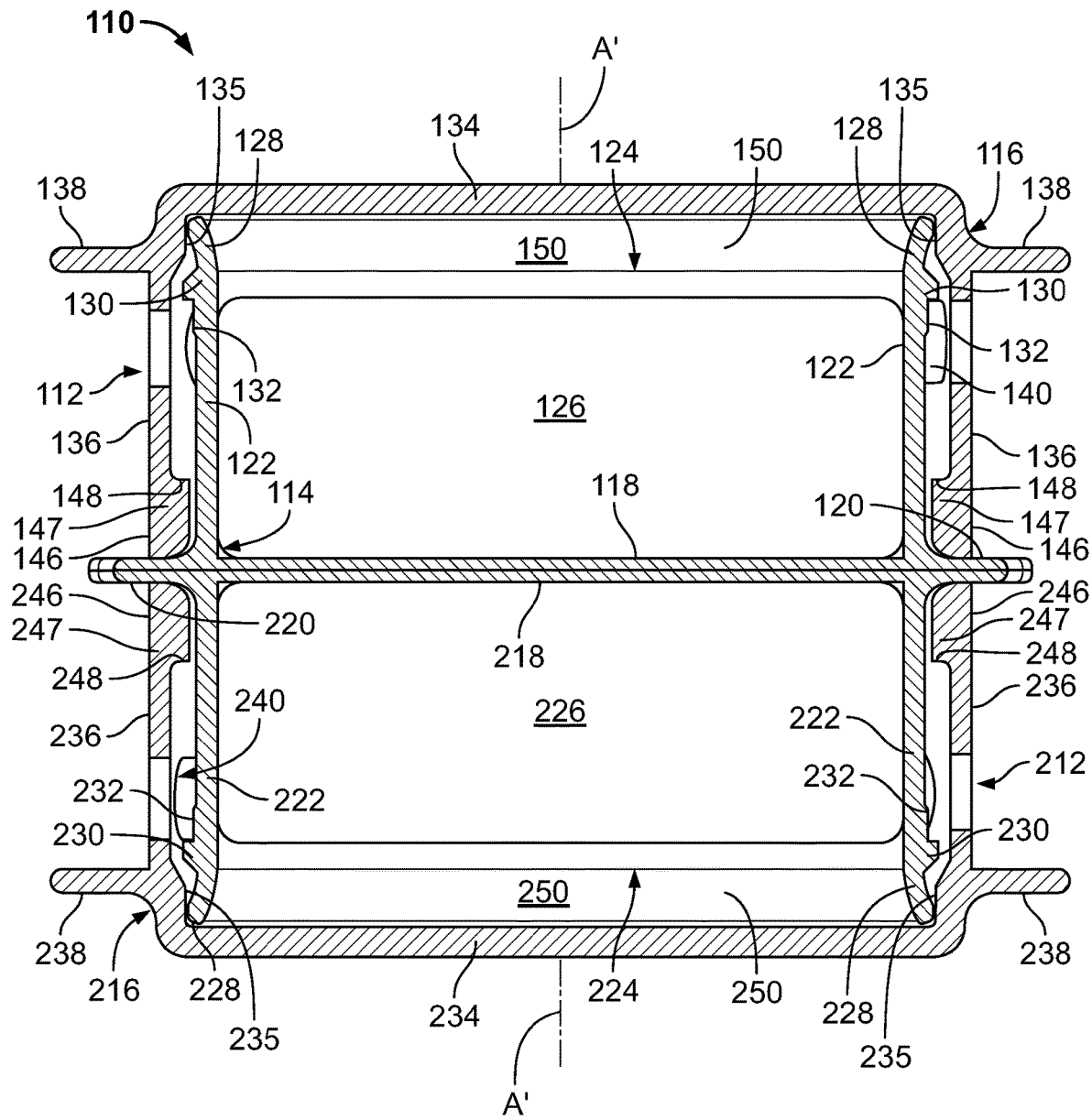
FIG. 9 is a cross-sectional view, taken along section line 9-9 in FIG. 8 and looking in the direction of the arrows, showing the interior of the scent dispenser of FIG. 8 when it is in its closed (i.e., non-scent dispensing) position or condition.
Figure 10:
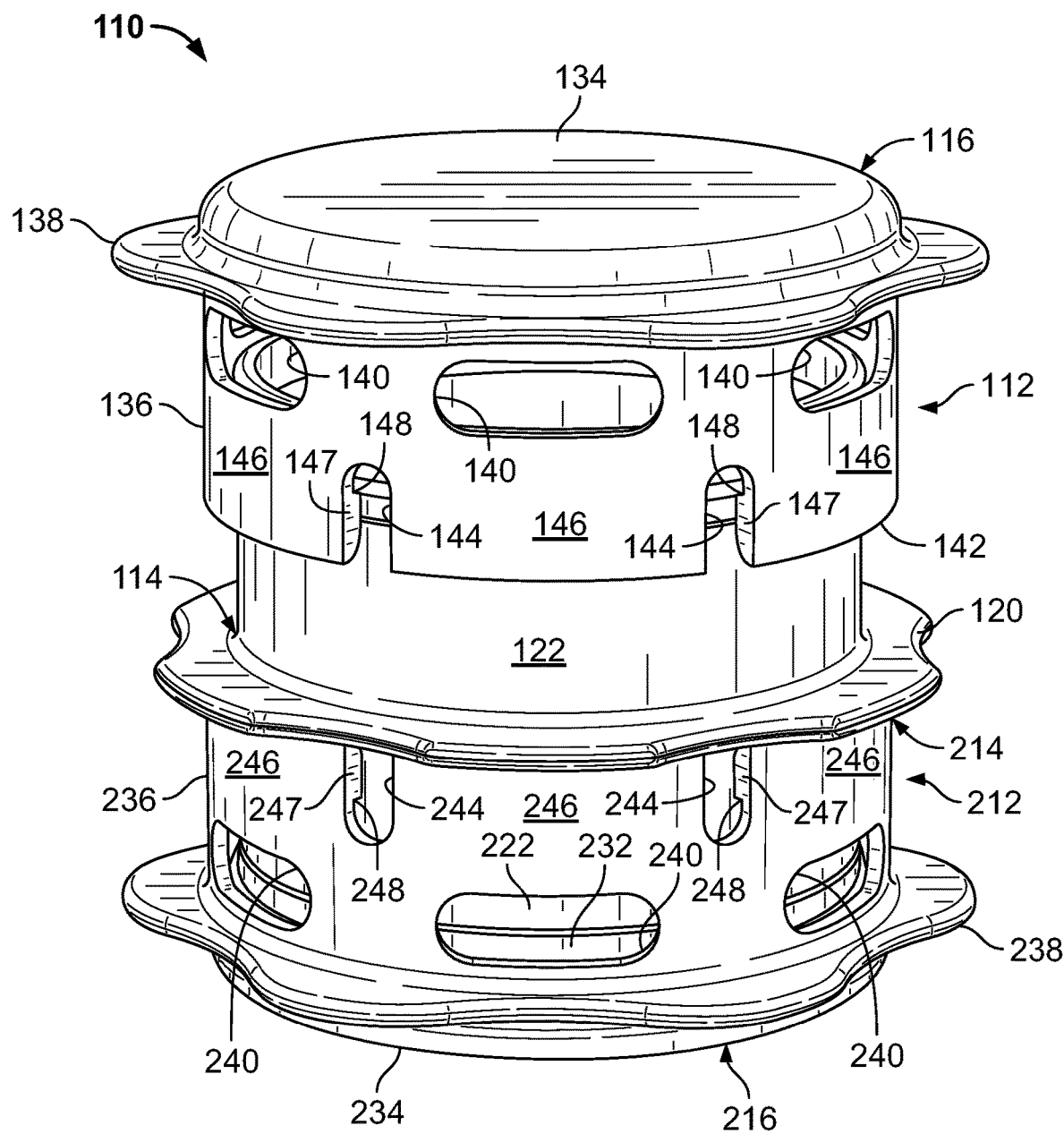
FIG. 10 is a top perspective view of the scent dispenser of FIG. 7, the dispenser being shown in a partially open (i.e., scent dispensing) position or condition and with one of its two covers in an expanded state, rather than in the contracted state depicted in FIG. 7.
Figure 11:
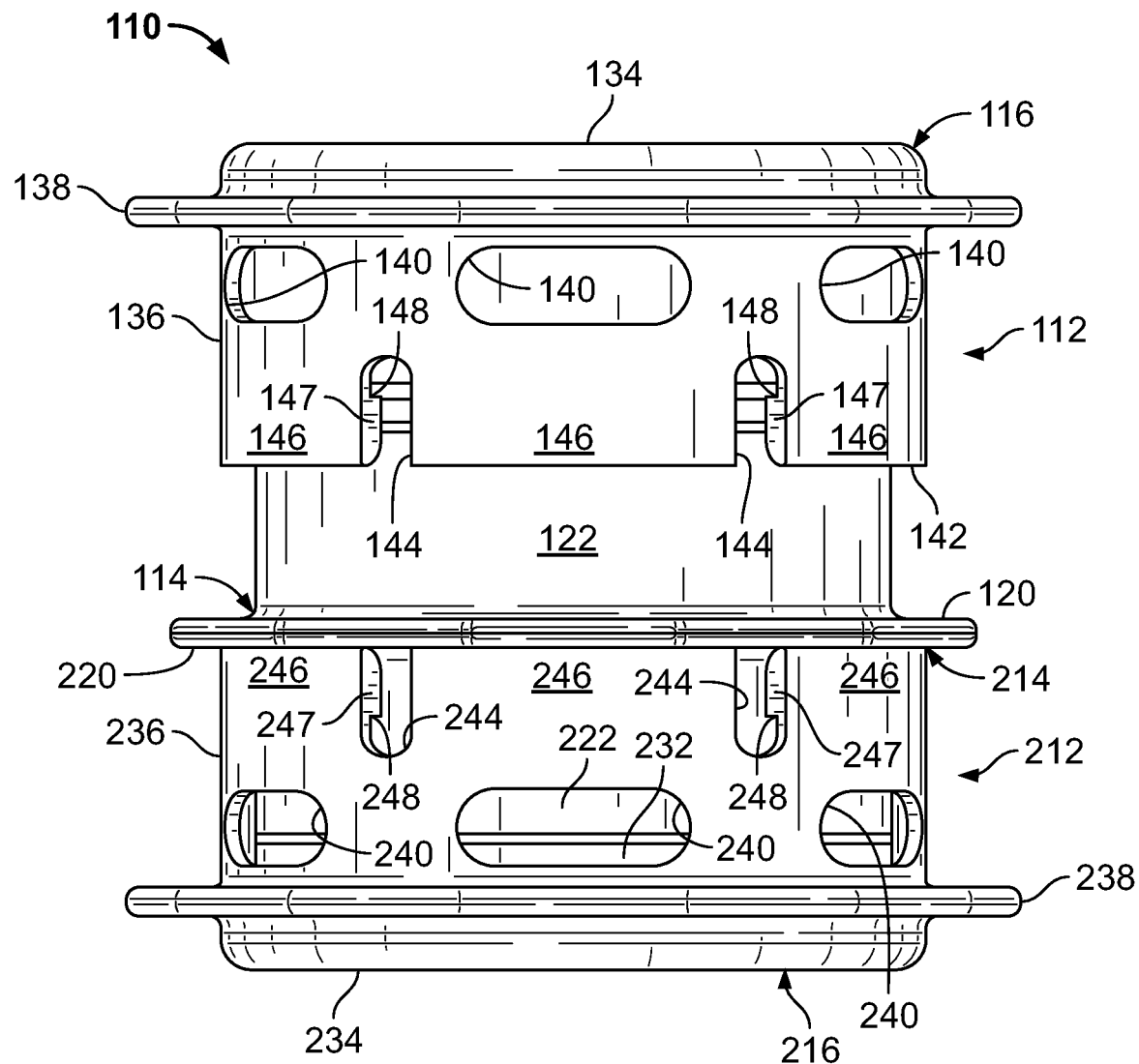
FIG. 11 is a side elevational view of the scent dispenser illustrated in FIG. 10.

The sidewall 136 of the cover 116 is also provided with a plurality of diffusion ports 140, each of which has a generally oval or oblong shape. The diffusion ports 140 are spaced apart around the circumference of the sidewall 136 in proximity to the annular flange 138. More particularly, the diffusion ports 140 are located on the side of the annular flange 138 opposite from the side that is proximate to the top surface 134 of the cover 116. When the housing 112 is in its closed position or condition as shown in FIGS. 7-9, the annular flanges 120, 138 project outwardly from the sidewall 136 of the cover 116 the same distance or approximately the same distance. However, in another embodiment, one of the flanges 120, 138 could project substantially farther than the other one.

The sidewall 136 has a lower rim 142 (see FIGS. 10-14) provided with a plurality of slots 144, each of which has a shape that resembles an inverted letter "U." The slots 144 are spaced apart around the circumference of the sidewall 136, in between the diffusion ports 140 to thereby form a plurality of flaps (i.e., fingers) 146. Each of the flaps 146 is provided with a radially inwardly projecting pad 147 forming a shoulder 148 (see especially FIGS. 9 and 14).

The slots 144 and diffusion ports 140 can be located at various different angular positions around the periphery (i.e., circumference) of the sidewall 136 and lower rim 142. For example, diffusion ports can be located at 90°, 180°, 270°, and 360° along the circumference of housing 112, while slots 144 may be located at 45°, 135°, 225° and 315°. While the exemplary embodiments described hereinabove have the diffusion ports 140 and slots 144 oriented in a symmetrical fashion about the circumference of base 114, in other embodiments the diffusion ports 140 and slots 144 can be oriented in an asymmetrical fashion.

With the cover 116 removed from the base 114 to thereby provide access to the interior chamber 124 of the housing 112, the insert 126 can be placed in the interior chamber 124, where it would rest on the bottom surface 118 of the base 114. Either before or after the aforementioned insertion step, any desired number of drops of a suitable odorant would be applied to the insert 126 from, for instance, a conventional droplet dispenser. After the aforementioned odorant application step, the cover 116 of the housing 112 would be applied to the base 114 and moved to its retracted position (see FIGS. 7-9), in which housing 112 would be in its closed position or condition. The application of the cover 116 to the base 114 is facilitated by the slots 144, which make the flaps 146 resilient enough to flex radially outwardly in response to contact by the flared upper rim 128 and the annular flange 130 of the base 114.

When the cover 116 is in its fully retracted position relative to the base 114 (i.e., when the housing 112 is in its closed position or condition), the upper rim 128 of the sidewall 122 of the base 114 contacts a radially inwardly extending flange 135 located at the juncture of the top surface 134 and sidewall 136 of cover 116 and cooperates with flange 135, which extends around the entire perimeter of sidewall 136, to form a water-tight or liquid-tight seal for the interior chamber 124. In other words, the upper rim 128 and the flange 135 function as sealing members. Also, when the cover 116 is in its fully retracted position, the diffusion ports 140 in its sidewall 136 are completely covered or blocked by the sidewall 122 of the base 114, whereby the interior chamber 124 is sealed off from the outside environment.

Conversely, when the cover 116 is in its fully extended position relative to the base 114 (i.e., when the housing 112 is in its open position or condition), the annular band 132 creates a slight friction fit with the pads 147 on the flaps 146 at the lower rim 142 of the cover 116 to thereby maintain the cover 116 in its completely extended position and, consequently, the housing 112 in its completely open position or condition in which the diffusion ports 140 are completely uncovered. When the housing 112 is in its aforesaid completely open position or condition, scent can also flow out of the slots 144, thereby increasing the amount of scent being dispensed. Because some of the slots 144 are angularly aligned with the diffusion ports 140 and some of the slots 144 are located between the diffusion ports 140 along the perimeter (i.e., circumference) of sidewall 136, scent is released or absorbed more evenly around entire the circumference of the housing 112.

It should be noted that the frictional forces produced by the contact between the annular band 132 and the pads 147 can be calculated such that the cover 116 is automatically maintained at any one of a number of variable (i.e., intermediate) positions relative to the base 114, thereby permitting a user to vary the uncovered portions of the diffusion ports 140 so as to regulate the dispersion of the scent emanating from the housing 112. Certain intermediate positions permit scent to flow out of slots 144 in addition to diffusion ports 140. Likewise, the cover 116 may be rotated by a user to adjust it to any number of variable rotational positions relative to the base 114 to control the directionality of the scent emanating from the housing 112 through the diffusion ports 140 and/or the slots 144. The size, shape and number of the diffusion ports 140 and the slots 144 can be selected so as to further dictate the degree to which scent emanates from housing 112 when open, either completely or partially. The same parameters can also be manipulated to change the scent dispersion pattern of housing 112 when either completely or partially open. It should also be noted that the fully extended position of the cover 116 is delimited by the annular flange 130 on the sidewall 122 of the base 114, which functions as a stop when contacted by the shoulders 148 on the flaps 146 formed along the lower rim 142 of the cover 116. The annular flange 130 may also cooperate with the shoulders 148 to prevent the removal of the cover 116 from the base 114 or to make such removal possible, but difficult, or even easy.

When, for example, the insert 126 is made from a hydrophilic polyurethane material, the insert 126 would capture the odorant and allow odorant molecules, which are polar or near polar, to spread throughout the hydrophilic polyurethane material of the insert 126. With the housing 112 in its closed position or condition as shown in FIGS. 7-9, evaporation of the odorant molecules will be contained within the housing 112, thereby filling a headspace 150 (see FIG. 9) between the insert 126 and the top surface 134 of the cover 116. Because any such hydrophilic polyurethane material (it being of medical grade) would have been reacted with water, the odorant scent released from the insert 126 into the headspace 150 of the housing 112 will not be adulterated by an additive in the manufacturing process. The result is that when the housing 112 is put in its open position or condition by moving the cover 116 to its extended position relative to the base 114 (see FIGS. 10-14), the insert 126 performs a scent-emitting function, whereby a faithful iteration of the original odorant scent will be released from the housing 112 for sampling or other purposes. In other words, the aforementioned sampling step is carried out in an environment in which essentially ambient air contains scent molecules, but no liquid. Thus, the scent dispenser 110 allows scents to be stored, transported and/or sampled in a non-liquid form.

Figure 12:
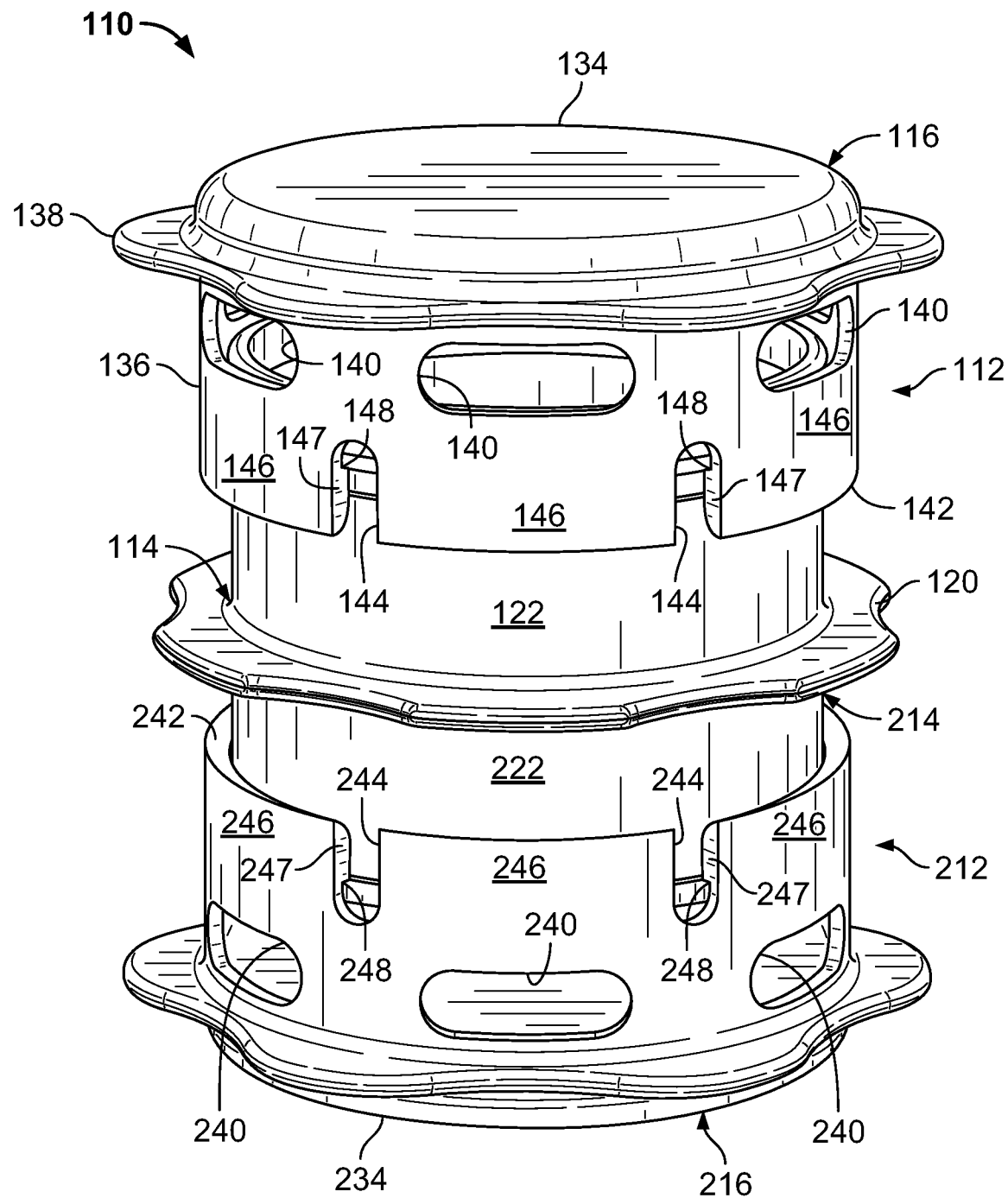
FIG. 12 is a top perspective view of the scent dispenser of FIG. 7, the dispenser being shown in a fully open (i.e., scent dispensing) position or condition and with both of its two covers in expanded states, rather than in the contracted states depicted in FIG. 7.
Figure 13:
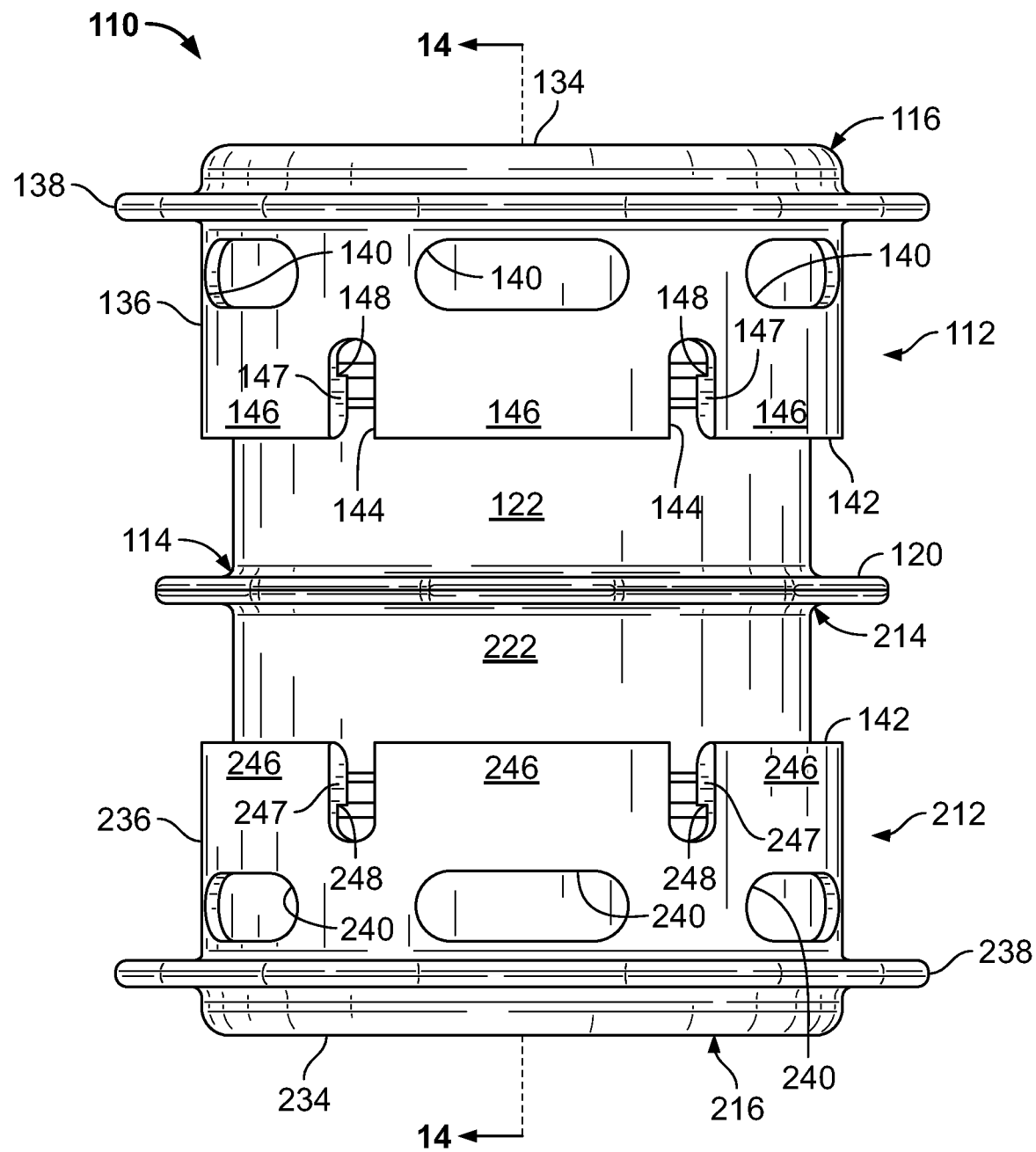
FIG. 13 is a side elevational view of the scent dispenser illustrated in FIG. 12.
Figure 14:
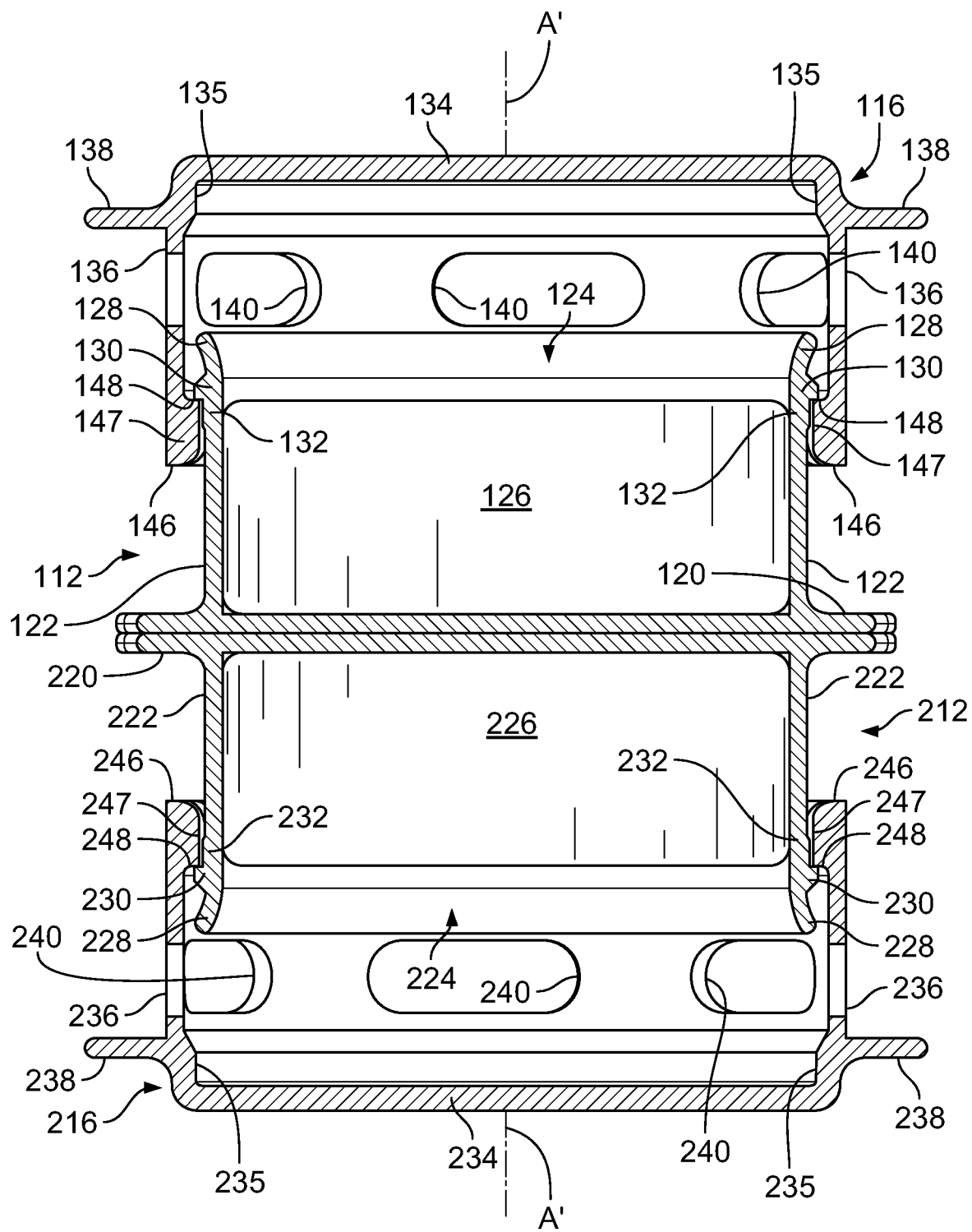
FIG. 14 is a cross-sectional view, taken along section line 14-14 in FIG. 13 and looking in the direction of the arrows, showing the interior of the scent dispenser of FIG. 13 when it is in its fully open (i.e., scent dispensing) position or condition.

Turning now to the housing 212, it is formed by a base 214 and a cover 216, which is slidably movable along the same longitudinal axis (i.e., the longitudinal axis A' in FIGS. 9 and 14) as housing 112 in a rectilinear (i.e., axial), telescoping-like fashion relative to the base 214, between a retracted position (see FIGS. 7-11) and a completely extended position (see FIGS. 12-14). The base 214 and the cover 216 are also rotatable relative to one another as indicated above, whereby they may assume various different rotational orientations relative to each other.

The base 214, which can, for example, be molded monolithically from polypropylene or any other suitable material, includes a substantially flat bottom surface 218 (see FIGS. 9 and 14) and an annular flange 220 projecting radially outwardly from the bottom surface 218 of the base 214. The flange 220, which has a scalloped design to facilitate gripping by a user's hand, extends around the entire circumference of the base 214. While the flange 220 is shown as being separate and discrete from the flange 120 and attached thereto by any suitable means (e.g., by gluing, ultrasonic welding, etc.), the flanges 120, 220 could also be contiguous with one another and formed as a single piece (e.g., produced from the same mold monolithically), whereby they would be common to both of the housings 112, 212. In another embodiment, the flanges 120, 220 would be releasably attached to one another, whereby the housings 112, 212 could remain attached for use as a tandem unit, or they could be detached from one another for use as two individual units.

The base 214 also includes a solid (i.e., uninterrupted), cylindrical sidewall 222 extending upwardly from the bottom surface (i.e., support surface) 218 of the base 214 and cooperating with the bottom surface 218 of the base 214 to form an interior chamber 224 (see FIGS. 9 and 14) having an open upper end and a lower end that is closed by the bottom surface 218 of the base 214. The interior chamber 224 is sized and shaped to receive a round, disc-like insert 226 (see FIGS. 9 and 14) made of foam or any other suitable material (e.g., a piece of medical grade hydrophilic polyurethane, preferably non-reticulated and about 3/16 of an inch in thickness) adapted to absorb or adsorb a volatile scented substance.

The sidewall 222 is provided with an outwardly flared rim 228 (see FIGS. 9 and 14) and an annular flange 230 (see FIGS. 9 and 14), which projects radially outwardly from the sidewall 222 in proximity to the upper rim 228. Both the upper rim 228 and the annular flange 230 extend around the entire circumference of the sidewall 222. An annular band 232 also extends around the entire circumference of the sidewall 222. The annular band 232 is positioned on the sidewall 222 adjacent the annular flange 230. More particularly, the annular band 232 is located on the side of the annular flange 230 opposite from the side that is proximate the upper rim 228. The annular band 232 projects radially outwardly from the sidewall 222 a distance that is less than the distance that the annular flange 230 projects from the sidewall 222.

The cover 216, which can also be molded monolithically from polypropylene or any other suitable material, has a substantially flat top surface (i.e., closed end) 234 (see FIGS. 8 and 9) and a cylindrical sidewall 236 extending downwardly from the top surface 234 of the cover 216. An annular flange 238 projects radially outwardly from the sidewall 236 of the cover 216. The flange 238, which has a scalloped design to facilitate gripping by another hand of the user, extends around the entire circumference of the sidewall 236.

The sidewall 236 of the cover 216 is also provided with a plurality of diffusion ports 240, each of which has a generally oval or oblong shape. The diffusion ports 240 are spaced apart around the circumference of the sidewall 236 in proximity to the annular flange 238. More particularly, the diffusion ports 240 are located on the side of the annular flange 238 opposite from the side that is proximate to the top surface 234 of the cover 216. When the housing 212 is in its closed position or condition as shown in FIGS. 7-9, the annular flanges 220, 238 project outwardly from the sidewall 236 of the cover 216 the same distance or approximately the same distance. However, in another embodiment, one of the flanges 220, 238 could project substantially farther than the other one.

The sidewall 236 has a lower rim 242 (see FIGS. 12-14) provided with a plurality of slots 244, each of which has a shape that resembles the letter "U." The slots 244 are spaced apart around the circumference of the sidewall 236, in between the diffusion ports 240 to thereby form a plurality of flaps (i.e., fingers) 246. Each of the flaps 246 is provided with a radially inwardly projecting pad 247 forming a shoulder 248 (see especially FIGS. 9 and 14).

The slots 244 and diffusion ports 240 can be located at various different angular positions around the periphery (i.e., circumference) of the sidewall 236 and lower rim 242. For example, diffusion ports 240 can be located at 90°, 180°, 270°, and 360° along the circumference of housing 212, while slots 244 may be located at 45°, 135°, 225° and 315°. While the exemplary embodiments described hereinabove have the diffusion ports 240 and slots 244 oriented in a symmetrical fashion about the circumference of base 214, in other embodiments the diffusion ports 240 and slots 244 can be oriented in an asymmetrical fashion.

With the cover 216 removed from the base 214 to thereby provide access to the interior chamber 224 of the housing 212, the insert 226 can be placed in the interior chamber 224, where it would rest on the bottom surface 218 of the base 214. Either before or after the aforementioned insertion step, any desired number of drops of a suitable odorant would be applied to the insert 226 from, for instance, a conventional droplet dispenser. After the aforementioned odorant application step, the cover 216 of the housing 212 would be applied to the base 214 and moved to its retracted position (see FIGS. 7-9), in which the housing 212 would be in its closed position or condition. The application of the cover 216 to the base 214 is facilitated by the slots 244, which make the flaps 246 resilient enough to flex radially outwardly in response to contact by the flared upper rim 228 and the annular flange 230 of the base 214.

When the cover 216 is in its fully retracted position relative to the base 214 (i.e., when the housing 212 is in its closed position or condition), the upper rim 228 of the sidewall 222 of the base 214 contacts a radially inwardly extending flange 235 located at the juncture of the top surface 234 and sidewall 236 of cover 216 and cooperates with flange 235, which extends around the entire perimeter of sidewall 236, to form a water-tight or liquid-tight seal for the interior chamber 224. In other words, the upper rim 228 and the flange 235 function as sealing members. Also, when the cover 216 is in its fully retracted position, the diffusion ports 240 in its sidewall 236 are completely covered or blocked by the sidewall 222 of the base 214, whereby the interior chamber 224 is sealed off from the outside environment.

Conversely, when the cover 216 is in its completely extended position relative to the base 214 (i.e., when the housing 212 is in its open position or condition), the annular band 232 creates a slight friction fit with the pads 247 on the flaps 246 at the lower rim 242 of the cover 216 to thereby maintain the cover 216 in its completely extended position and, consequently, the housing 212 in its completely open position or condition in which the diffusion ports 240 are completely uncovered. When the housing 212 is in its aforesaid completely open position or condition, scent can also flow out of the slots 244, thereby increasing the amount of scent being dispensed. Because some of the slots 244 are angularly aligned with the diffusion ports 240 and some of the slots 244 are located between the diffusion ports 240 along the perimeter (i.e., circumference) of sidewall 236, scent is released or absorbed more evenly around the entire circumference of the housing 212.

It should be noted that the frictional forces produced by the contact between the annular band 232 and the pads 247 can be calculated such that the cover 216 is automatically maintained at any one of a number of variable (i.e., intermediate) positions relative to the base 214, thereby permitting a user to vary the uncovered portions of the diffusion ports 240 so as to regulate the dispersion of the scent emanating from the housing 212. Certain intermediate positions permit scent to flow out of slots 244 in addition to diffusion ports 240.

Likewise, the cover 216 may be rotated by a user to adjust it to any number of variable rotational positions relative to the base 214 to control the directionality of the scent emanating from the housing 212 through the diffusion ports 240 and/or the slots 244. The size, shape and number of the diffusion ports 240 and the slots 244 can be selected so as to further dictate the degree to which scent emanates from housing 212 when open, either completely or partially. The same parameters can also be manipulated to change the scent dispersion pattern of housing 212 when either completely or partially open. It should also be noted that the fully extended position of the cover 216 is delimited by the annular flange 230 on the sidewall 222 of the base 214, which functions as a stop when contacted by the shoulders 248 on the flaps 246 formed along the lower rim 242 of the cover 216. The annular flange 230 may also cooperate with the shoulders 248 to prevent the removal of the cover 216 from the base 214 or to make such removal possible, but difficult, or even easy.

When, for example, the insert 226 is made from a hydrophilic polyurethane material, the insert 226 would capture the odorant and allow odorant molecules, which are polar or near polar, to spread throughout the hydrophilic polyurethane material of the insert 226. With the housing 212 in its closed position or condition as shown in FIGS. 7-9, evaporation of the odorant molecules will be contained within the housing 212, thereby filling a headspace 250 (see FIG. 9) between the insert 226 and the top surface 234 of the cover 216. Because any such hydrophilic polyurethane material (it being of medical grade) would have been reacted with water, the odorant scent released from the insert 226 into the headspace 250 of the housing 212 will not be adulterated by an additive in the manufacturing process. The result is that when housing 212 is put in its open position or condition by moving the cover 216 to its extended position relative to the base 214 (see FIGS. 12-14), the insert 226 performs a scent-emitting function, whereby a faithful iteration of the original odorant scent will be released from the housing 212 for sampling or other purposes. In other words, the aforementioned sampling step is carried out in an environment in which essentially ambient air contains scent molecules, but no liquid. Thus, the scent dispenser 110 allows scents to be stored, transported and/or sampled in a non-liquid form.

While the inserts 126, 226 have been described with reference to a specific embodiment thereof, it should be understood by those skilled in the art that various changes may be made and equivalents may be substituted without departing from the true spirit and scope of the present invention. For instance, the scent dispenser 110 is adapted for use with other types of scent capturing and diffusing media such as the scent cell disclosed in U.S. Patent Application Publication No. 2017/0312380 (see especially Paragraphs [0048] to [0050], U.S. Pat. No. 8,544,766 (see especially Column 6, lines 30-59) and U.S. Pat. No. 6,617,014, all of which patent publications are incorporated herein by reference in their entireties. In addition, many modifications may be made to the embodiment of FIGS. 7-14 described herein to adapt it to a particular situation, use or application without departing from the overall objective, spirit and/or scope of the present invention. For instance, the inserts 126, 226 can be replaced by, for example, a scent cartridge adapted to absorb and/or adsorb a volatile scented substance, while allowing the ready passage of air therethrough. In some embodiments, the scent cartridge would contain an amount of volatile scented substance, such as those used in perfumes, for attracting game, for calming a pet, as diet aids, for aroma therapy, for medical applications, or for other uses which are known or may become known, such as providing cannabis-derived or hemp-derived scents, fragrances, etc. In some embodiments, the scent cartridge would be designed such that the scented substance may be added directly to the cartridge to replenish or change the scent.

By way of further example, the inserts 126, 226 may be made of any material that can carry and release volatile scented substances. In some embodiments, it could be made of an absorbent fibrous material or closed cell foam having air passages penetrating therethrough. In other embodiments, the inserts 126, 226 could be made of an open-cell foam that presents an appreciable ratio of surface area to volume of foam, with higher ratios typically being preferred. In such embodiments, the foam may be a hydrophilic foam or have a hydrophilic material exposed at the surfaces of its cells. Other suitable embodiments could utilize an open-cell foam composite made of substantially hydrophobic foam to provide structure to the composite and substantially hydrophilic foam exposed at the surfaces of its cells, such as the foam described in U.S. Pat. No. 6,617,014, whose disclosure is incorporated herein by reference in its entirety.

In yet another embodiment, the inserts 126, 226 may comprise a nonwoven fibrous material substrate coated with, for example, a substantially hydrophilic foam coating which is exposed at the surface and in interstitial spaces within the nonwoven fibrous material. The interstitial spaces within the nonwoven fibrous material form air passages penetrating therethrough to allow the flow of air. Examples of suitable nonwoven fibrous materials include, without limitation, cotton, felt, silk, or combinations thereof. As will be recognized by persons of ordinary skill in the relevant art, such embodiments would be useful when the volatile scented substances employed to impart scent or alternative odor to the inserts 126, 226 are of the types that may react with and degrade some hydrophobic foams (see, e.g., U.S. Pat. No. 8,544,766, which is incorporated herein by reference in its entirety). One possible process for producing such inserts involves contacting a substrate of nonwoven fibrous material with a prepolymer emulsion and then polymerizing or curing the emulsion. By way of further example, the substrate can be dipped or immersed in the prepolymer emulsion, which can also be applied by brushing, spraying or otherwise coating onto the substrate. In an embodiment of such a process, the substrate of nonwoven fibrous material may be provided as a sheet or block and then sprayed with the prepolymer emulsion, followed by polymerization or curing of the emulsion to form the substantially hydrophilic foam on the nonwoven fibrous substrate. The substrate can then be cut into appropriately sized and shaped pieces to produce the inserts 126, 226, which would have the characteristics desired of this particular embodiment.

In operation, the cover 116 of the housing 112 can be moved away (i.e., extended) from the base 114 to expose the diffusion ports 140 in the sidewall 122 of the base 114. In such an open condition or position of the housing 112, desirable scents can flow from the scent means 126 of the housing 112 to the surrounding environment. The type of scent emitted from the housing 112 will be dependent upon the volatile substance loaded into the scent means 126.

Independent of the open or closed condition of the housing 112, the cover 216 of the housing 212 can be moved away (i.e., extended) from the base 214 to expose the diffusion ports 240 in the sidewall 222 of the base 214. In such an open condition or position of the housing 212, desirable scents can flow from the scent means 226 of the housing 212 to the surrounding environment. Depending upon the type of volatile substance loaded into the scent means 226, a scent that is the same as or different from the scent emanating from the housing 112 will be emitted from the housing 212.

In a further mode of operation, no volatile substance is loaded into the scent means 226 of the housing 212, in which case the housing 212 functions in an odor-absorbing manner or mode when it is in its open condition or position. In such a condition, undesirable odors in the surrounding environment can flow into the scent means 226. If the scent means 126 of the housing 112 is also devoid of a volatile substance, then both of the housings 112, 212 will function in odor-absorbing manners or modes when they are in their open conditions or positions.

It should be understood that the embodiments described herein are merely exemplary in nature and that a person skilled in the art may make many variations and modifications thereto without departing from the scope of the present invention. For example, in certain embodiments, a scent dispenser/absorber, which can be either of the embodiments disclosed herein (i.e., the single scent dispenser/absorber of FIGS. 1-6 or the dual scent dispenser/absorber of FIGS. 7-14) or some other scent dispensing device (e.g., the devices disclosed in U.S. Pat. No. 8,544,766, which patent has already been incorporated by reference herein) may be equipped with conventional Radio Frequency Identification (RFID) technology to collect, retrieve, store, and process data related to their use, thereby transforming such devices into so-called "intelligent devices." These "intelligent" or "smart" scent dispensing/absorbing devices would typically, but not necessarily, comprise the following systems: a communication system; a processor; a sensor pack; and a power system. The communication system could be Wi-Fi, Bluetooh LE, or near field (NFC, RFID). The processor would serve the function of local data logging and managing the communications processes. The sensor pack could include accelerometers, contact sensors, GPS, magnetic or flow, the choice depending upon the size of the device and costs. The power system could be: (i) an onboard battery, remotely powered like an RFID or wireless charger; (ii) an energy harvesting device that is powered by each press; or (iii) externally powered by a cord-like USB. The whole system would likely need to be very low power and therefore its functionality could be derived from a single chip. The sensors could be set to report back pumps, output flow, location, time, temperature and diagnostic information from the processor. By way of further example, the data processed by such "intelligent" scent dispensers/absorbers could include, for instance, when the scent dispenser was opened, how long it was left open, the identity of the scent and user of the device, etc. All such variations and modifications, including those discussed above, are intended to be included within the scope of the invention described in the accompanying claims.

We claim:

1. A device adapted to function as a scent dispenser/absorber, comprising:
    a base having a longitudinal axis, a support surface, and a first sidewall projecting from said support surface and extending around said longitudinal axis to define a first perimeter, said first sidewall having a first rim extending around said first perimeter and projecting radially outward relative to said longitudinal axis of said base at an end of said first sidewall distal to said support surface of said base; and
    a cover slidably mounted on said base in a coaxial relationship relative to said longitudinal axis of said base, said cover having a closed end, a second sidewall projecting from said closed end and extending around said longitudinal axis to define a second perimeter, said second sidewall having a second rim at an end of said second sidewall distal to said closed end, a flange projecting in a radially inward direction from said second sidewall proximate said closed end of said cover and extending around said second perimeter of said second sidewall, a plurality of spaced diffusion ports in said second sidewall between said second rim and said flange, and a plurality of slots formed in said second rim of said second sidewall, said plurality of slots extending from said second rim towards said closed end, said cover cooperating with said base to define an interior chamber of said device, said cover being mounted on said base such that said cover and said base are movable relative to each other along said longitudinal axis between a closed position, in which said interior chamber of said device is isolated from the outside environment surrounding said device as a result of said first rim of said base being in sealing contact with said flange of said cover, and an open position, in which said interior chamber of said device is in communication with the outside environment surrounding said device via said diffusion ports and said slots of said cover as a result of said first rim of said base being out of sealing contact with said flange of said cover.

2. The device of claim 1, further comprising a first scalloped flange projecting radially outward from said closed end of said cover and a second scalloped flange projecting radially outward from said support surface of said base.

3. The device of claim 1, wherein said slots in said second sidewall of said cover define a plurality of flaps configured to flex radially outward in response to contact by said first rim of said first sidewall of said base to rotate relative to said base, said cover being adapted to rotate relative to said base about said longitudinal axis.

4. The device of claim 3, wherein each of said flaps includes an inwardly projecting pad forming a shoulder.

5. The device of claim 4, wherein said base further includes an annular band extending around said first perimeter of said base, said annular band configured to contact said pads such that frictional forces maintain said device in one or more variable positions.

6. The device of claim 1, further comprising a scent-dispensing means positioned in said interior chamber, whereby scents fill said interior chamber of said device when said device is in said closed position.

7. The device of claim 1, further comprising a scent-absorbing insert positioned in said interior chamber of said device, whereby undesirable scents can flow into said scent-absorbing insert when said device is in said open position.

8. The device of claim 1, wherein said slots in said second sidewall are arranged asymmetrically about said second perimeter.

9. The device of claim 8, wherein said diffusion ports in said second sidewall are arranged asymmetrically about said second perimeter.

10. The device of claim 1, wherein said slots in said second sidewall are arranged symmetrically about said second perimeter.

11. The device of claim 10, wherein said diffusion ports in said second sidewall are arranged symmetrically about said second perimeter.

12. A device adapted to function as a scent dispenser and/or scent absorber, comprising:
- a base having a longitudinal axis, a first support surface, and a first sidewall projecting from said first support surface in a first direction and extending around said longitudinal axis to define a first perimeter, said first sidewall having a first rim extending around said first perimeter and projecting radially outward relative to said longitudinal axis of said base at an end of said first sidewall distal to said first support surface of said base, a second support surface positioned adjacent and in a back-to-back relationship with said first support surface, a second sidewall projecting from said second support surface in a second direction, opposite said first direction, and extending around said longitudinal axis to define a second perimeter, said second sidewall having a second rim extending around said second perimeter and projecting radially outward relative to said longitudinal axis of said base at an end of said second sidewall distal to said second support surface of said base;
- a first cover slidably mounted on said base in a coaxial relationship relative to said longitudinal axis of said base, said first cover having a first closed end, a third sidewall projecting from said first closed end and extending around said longitudinal axis to define a third perimeter, said third sidewall having a third rim at a first open end of said third sidewall distal to said first closed end, a first flange projecting in a radially inward direction from said third sidewall proximate said first closed end of said first cover and extending around said third perimeter of said third sidewall, a first plurality of spaced diffusion ports in said third sidewall between said third rim and said first flange, and a first plurality of slots formed in said third rim of said third sidewall, said first plurality of slots extending from said third rim towards said first closed end, said first cover cooperating with said base to define a first interior chamber of said device, said first cover being mounted on said base such that said first cover and said base are movable relative to each other along said longitudinal axis between a closed position, in which said first interior chamber of said device is isolated from the outside environment surrounding said device as a result of said first rim of said base being in sealing contact with said first flange of said first cover, and an open position, in which said first interior chamber of said device is in communication with the outside environment surrounding said device via said first plurality of diffusion ports and said first plurality of slots of said first cover as a result of said first rim of said base being out of sealing contact with said first flange of said first cover; and
- a second cover slidably mounted on said base in a coaxial relationship relative to said longitudinal axis of said base, said second cover having a second closed end, a fourth sidewall projecting from said second closed end and extending around said longitudinal axis to define a fourth perimeter, said fourth sidewall having a fourth rim at a second open end of said fourth sidewall distal to said second closed end, a second flange projecting in a radially inward direction from said fourth sidewall proximate said second closed end of said second cover and extending around said fourth perimeter of said fourth sidewall, a second plurality of spaced diffusion ports in said fourth sidewall between said fourth rim and said second flange, and a second plurality of slots formed in said fourth rim of said fourth sidewall, said second plurality of slots extending from said fourth rim towards said second closed end, said second cover cooperating with said base to define a second interior chamber of said device, said second cover being mounted on said base such that said second cover and said base are movable relative to each other along said longitudinal axis between a closed position, in which said second interior chamber of said device is isolated from the outside environment surrounding said device as a result of said second rim of said base being in sealing contact with said second flange of said second cover, and an open position, in which said second interior chamber of said device is in communication with the outside environment surrounding said device via said second plurality of diffusion ports and said second plurality of slots of said second cover as a result of said second rim of said base being out of sealing contact with said second flange of said second cover.

13. The device of claim 12, wherein said first and second support surfaces of said base are formed integrally with one another.

14. The device of claim 12, wherein said first and second support surfaces of said base are releasably attached to one another, whereby said device can be separated into a pair of housings.

15. The device of claim 12, further comprising a first scalloped flange projecting radially outward from said first closed end of said first cover, a second scalloped flange projecting radially outward from said closed end of said second cover, and a third scalloped flange projecting radially outward from said first and second support surfaces of said base.

16. The device of claim 12, wherein said first interior chamber includes a first scent-dispensing/absorbing means and said second interior chamber each includes a second scent-dispensing/absorbing means.

17. The device of claim 16, wherein at least one of said scent-dispensing/absorbing means is adapted to dispense desirable fragrances.

18. The device of claim 16, wherein at least one of said scent-dispensing/absorbing means is adapted to absorb undesirable odors.

19. The device of claim 17, wherein both of said scent-dispensing/absorbing means are adapted to dispense a common fragrance.

20. The device of claim 17, wherein one of said scent-dispensing/absorbing means is adapted to dispense a first fragrance and the other of said scent-dispensing/absorbing means is adapted to dispense a second fragrance, which is different from said first fragrance.

\* \* \* \* \*